United States Patent
Zhang et al.

(10) Patent No.: US 11,214,612 B2
(45) Date of Patent: Jan. 4, 2022

(54) ANTI-GLIADIN ANTIBODIES, ENCODING NUCLEIC ACIDS AND METHODS OF DETECTING GLIADIN

(71) Applicant: Nima Acquisition, LLC, Northfield, IL (US)

(72) Inventors: Jingqing Zhang, Hayward, CA (US); Shireen Taleghani Yates, San Francisco, CA (US); Scott Erik Sundvor, San Francisco, CA (US); Alim Seit-Nebi, San Diego, CA (US)

(73) Assignee: Nima Acquisition, LLC, Northfield, IL (US)

( * ) Notice: Subject to any disclaimer, the term of this patent is extended or adjusted under 35 U.S.C. 154(b) by 367 days.

(21) Appl. No.: 16/342,031

(22) PCT Filed: Oct. 12, 2017

(86) PCT No.: PCT/US2017/056409
§ 371 (c)(1),
(2) Date: Apr. 15, 2019

(87) PCT Pub. No.: WO2018/071718
PCT Pub. Date: Apr. 19, 2018

(65) Prior Publication Data
US 2021/0214422 A1    Jul. 15, 2021

Related U.S. Application Data

(60) Provisional application No. 62/408,301, filed on Oct. 14, 2016.

(51) Int. Cl.
*C07K 16/16* (2006.01)
*G01N 33/577* (2006.01)

(52) U.S. Cl.
CPC .......... *C07K 16/16* (2013.01); *G01N 33/577* (2013.01); *C07K 2317/622* (2013.01); *C07K 2317/92* (2013.01); *G01N 2333/415* (2013.01)

(58) Field of Classification Search
CPC .............. C07K 16/16; C07K 2317/622; G01N 2333/415
See application file for complete search history.

(56) References Cited

U.S. PATENT DOCUMENTS

| 2006/0002917 A1 | 1/2006 | Piper et al. |
| 2008/0171043 A1 | 7/2008 | Lin et al. |
| 2010/0015665 A1 | 1/2010 | Latham et al. |
| 2012/0114653 A1 | 5/2012 | Fox |
| 2013/0330348 A1 | 12/2013 | Lacy et al. |
| 2015/0018531 A1 | 1/2015 | Saunders et al. |

FOREIGN PATENT DOCUMENTS

AU    2006224660 A1    9/2006

OTHER PUBLICATIONS

Stratagene Catalog. p. 39, 1988.*
Caldas, C., et al. "Humanization of the anti-CD18 antibody 6.7: an unexpected effect of a framework residue in binding to antigen." Molecular Immunology 39.15 (2003): 941-952.
Du, J., et al. "Molecular basis of recognition of human osteopontin by 23C3, a potential therapeutic antibody for treatment of rheumatoid arthritis." Journal of molecular biology 382.4 (2008): 835-842.
Panka, D. J., et al. "Variable region framework differences result in decreased or increased affinity of variant anti-digoxin antibodies." Proceedings of the National Academy of Sciences 85.9 (1988): 3080-3084.
Xiang, J., et al. "Modification in framework region I results in a decreased affinity of chimeric anti-TAG72 antibody." Molecular immunology 28.1-2 (1991): 141-148.
International Search Report in PCT/US2017/056409, dated Mar. 7, 2018.
GENPEPT_PH1093, Ig heavy chain V region (clone S17.161)—mouse. GenPept Accession No. PH1093. Aug. 16, 1996 (online). (Retrieved on Dec. 21, 2017). Retrieved from the Internet: URL https://www.ncbi.nlm.nih.gov/protein/PH1093.
UNIPROTKB_N8ZSE2, Uncharacterized protein, UniProtKB Accession No. N8ZSE2, last modified: Jun. 26, 2013 (online). (Retrieved Mar. 29, 2019) Retrieved from the Internet: URL https://www.uniprot.org/uniprot/N8ZSE2.
Weiss, et al. "Gluten-sensitive enteropathy. Immunoglobulin G heavy-chain (Gm) allotypes and the immune response to wheat gliadin." The Journal of clinical investigation 72, No. 1 (1983): 96-101.
Morón et al. Sensitive detection of cereal fractions that are toxic to celiac disease patients by using monoclonal antibodies to a main immunogenic wheat peptide. The American journal of clinical nutrition. Feb. 1, 2008;87(2):405-14.

* cited by examiner

*Primary Examiner* — Robert S Landsman
(74) *Attorney, Agent, or Firm* — Quarles & Brady LLP

(57) ABSTRACT

The present invention provides anti-gliadin antibodies and antibody fragments, and polypeptides encoding the antibodies or fragment. Also disclosed are methods and Kits for the use of such antibodies, fragments, or polypeptides in detection of gliadin. Further provided are heavy chain and light chain variable sequences and associated sequences of complementarity-determining regions (CDRs).

17 Claims, 6 Drawing Sheets
Specification includes a Sequence Listing.

FIGURE 1

DNA AND AMINO ACID SEQUENCES FOR 13F6

Heavy chain: DNA sequence (405 bp)

Leader sequence-FR1-CDR1-FR2-CDR2-FR3-CDR3-FR4

ATGGCTTGGGTGTGGACCTTGCTATTCCTGATGGCAGCTGCCCAAAGTATCCAAGCACAGATCCAGT
TGGTGCAGTCTGGACCTGAGCTGAAGAAGCCTGGAGAGACAGTCAAGATCTCCTGCAAGGCTTCTGG
TTATACCTTCACAGACTATTCAATGCACTGGGTGAGGCAGGCTCCAGGAAAGGGTTTAAAGTGGATG
GGCTGGATAAACACTGAGACTGGTGAGCCAACATATGCAGATGACTTCAAGGGACGATTTGCCTTCT
CTTTGGAAACCTCTGCCAGCACTGCCTATCTGCAGATCAACAACCTCAAAAATGAGGACACGGCTAC
ACATTTCTGTGCTCCAAGTGTTGCCTGGTTTGCTTACTGGGGCCAAGGGACTCTGGTCACTGTCTCT
ACA

Heavy Chain: Amino acids sequence (135 aa)

Leader sequence-FR1-CDR1-FR2-CDR2-FR3-CDR3-FR4

MAWVWTLLFLMAAAQSIQAQIQLVQSGPELKKPGETVKISCKASGYTFTDYSMHWVRQAPGKGLKWM
GWINTETGEPTYADDFKGRFAFSLETSASTAYLQINNLKNEDTATHFCAPSVAWFAYWGQGTLVTVS
T

Light chain: DNA sequence (393 bp)

Leader sequence-FR1-CDR1-FR2-CDR2-FR3-CDR3-FR4

ATGAAGTTACCTGTTAGGCTGTTGGTGCTGATGTTCTGGATTCCTGCTTCCAGAAGTGATGTTTTGA
TGACCCAAACTCCACTCTCCCTGTCTGTCAGTCTTGGAGATCAGGCCTCCATCTCTTGTAGATCTAG
TCAGAGCATTGTACAGAGTAATGGAAACACCCATTTAGAATGGTTCTTACAGAAACCAGGCCAGTCT
CCAAAGCTCCTGATCTACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGAGTTTATTACTG
TTTTCAAGGTTCACATGTTCCATTCACGTTCGGCTCGGGGACAAAGTTGGAAATAAAA

Light chain: Amino acids sequence (131 aa)

Leader sequence-FR1-CDR1-FR2-CDR2-FR3-CDR3-FR4

MKLPVRLLVLMFWIPASRSDVLMTQTPLSLSVSLGDQASISCRSSQSIVQSNGNTHLEWFLQKPGQS
PKLLIYKVSNRFSGVPDRFSGSGSGTDFTLKISRVEAEDLGVYYCFQGSHVPFTFGSGTKLEIK

FIGURE 2

DNA AND AMINO ACID SEQUENCES FOR 14G11

Heavy chain: DNA sequence (405 bp)

Leader sequence-FR1-CDR1-FR2-CDR2-FR3-CDR3-FR4

ATGGCTTGGGTGTGGACCTTGCTATTCCTGATGGCAGCTGCCCAAAGTATCCAAGCACAGATCCAGT
TGGTGCAGTCTGGACCTGAGATGAAGAAGCCTGGAGAGACAGTCAAGATTTTTTGCAAGGCTTCTGG
TTATACCCTCACAGACTATTCAATGCACTGGGTGAAGCAGGCTCCAGGAAAGGGTTTAAAGTGGATG
GGCTGGATAAACACTGAGACTGGTGAGCCAACATATGCAGATGACTTCAAGGGACGGTGTGCCTTTT
CTTTGGAAACCTCTGTCAGCACTGCCTTTTTGCAGATCAACAACCTCAAAAATGAGGACATGGGAAC
ATATTTCTGTGCCTCCTCTGGGGCCTGGTTTAGTTACTGGGGCCAAGGGACTCTGGTCACTGTCTCT
GCA

Heavy chain: Amino acids sequence (135 aa)

Leader sequence-FR1-CDR1-FR2-CDR2-FR3-CDR3-FR4

MAWVWTLLFLMAAAQSIQAQIQLVQSGPEMKKPGETVKIFCKASGYTLTDYSMHWVKQAPGKGLKWM
GWINTETGEPTYADDFKGRCAFSLETSVSTAFLQINNLKNEDMGTYFCASSGAWFSYWGQGTLVTVS
A

Light chain: DNA sequence (393 bp)

Leader sequence-FR1-CDR1-FR2-CDR2-FR3-CDR3-FR4

ATGAAGTTGCCTGTTAGGCTGTTGGTGCTGATGTTCTGGATTCCTGCCTCCAGTGGTGATGTTTTGC
TGACCCAAACTCCACTCTCCCTGCCTGTCAGTCTTGGAGATCAAGCCTCCATCTCTTGCAGATCTAG
TCAGACCATTGTACAAATTAATGGAAACACCCATTTAGAATGGTTCCTGCAGAAACCAGGCCAGTCT
CCAAAGCTCCTGATCTATAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGAATTTATTACTG
CTTTCAAGGTTCACATGTTCCATTCACGTTCGGCTCGGGGACAAAGTTGGAAATAAAA

Light chain: Amino acids sequence (131 aa)

Leader sequence-FR1-CDR1-FR2-CDR2-FR3-CDR3-FR4

MKLPVRLLVLMFWIPASSGDVLLTQTPLSLPVSLGDQASISCRSSQTIVQINGNTHLEWFLQKPGQS
PKLLIYKVSNRFSGVPDRFSGSGSGTDFTLKISRVEAEDLGIYYCFQGSHVPFTFGSGTKLEIK

FIGURE 4
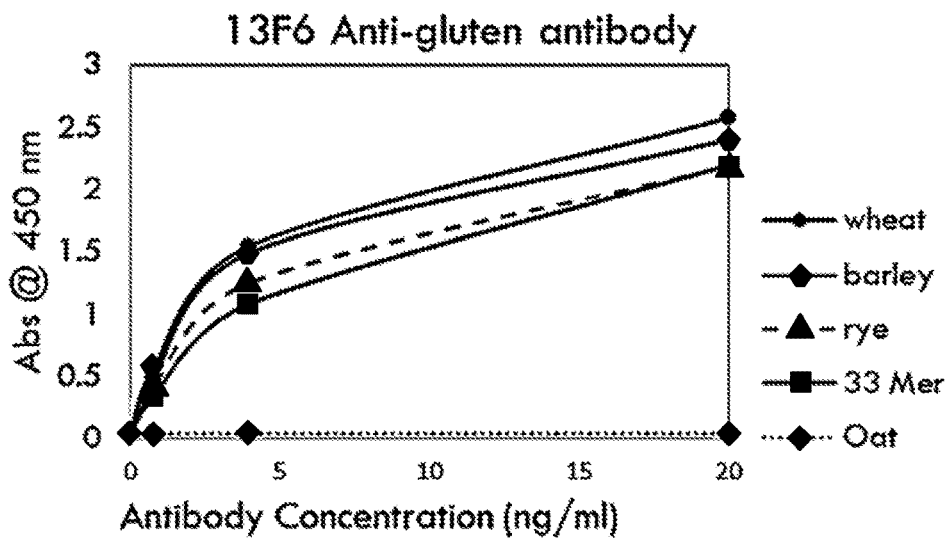
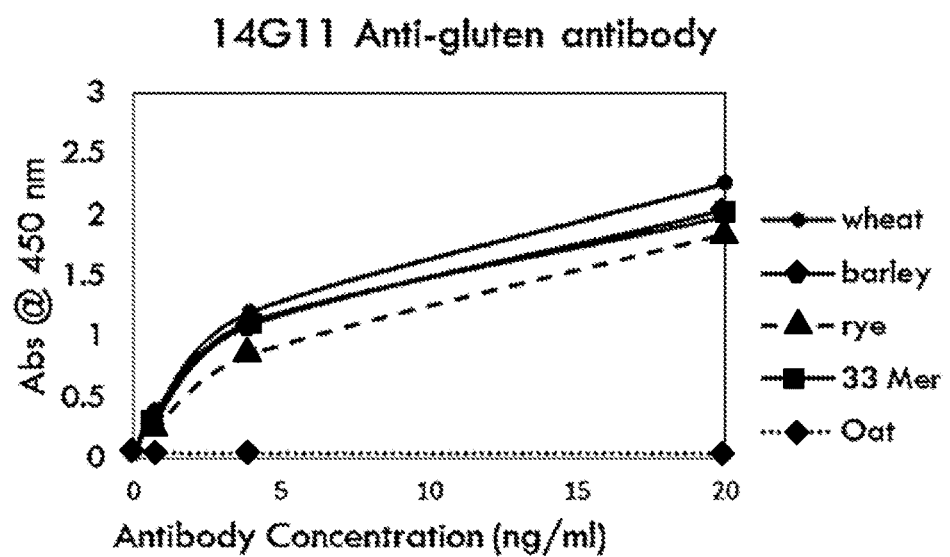
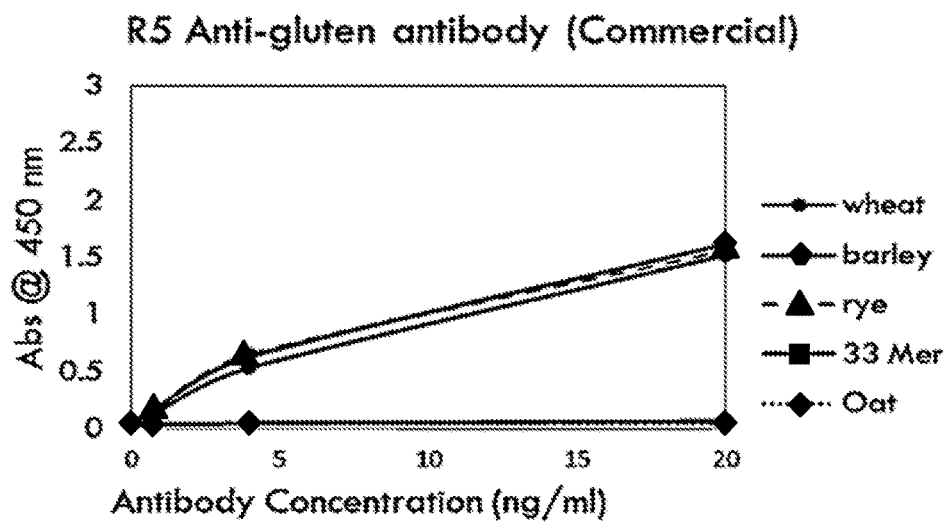

ANTI-GLIADIN ANTIBODIES, ENCODING NUCLEIC ACIDS AND METHODS OF DETECTING GLIADIN

RELATED APPLICATIONS

The Sequence Listing written in file Sequence_Listing_1126943.txt created on May 20, 2019, 28,672 bytes, machine format IBM-PC, MS-Windows operating system, is hereby incorporated by reference in its entirety for all purposes.

REFERENCE TO SUBMISSION OF A SEQUENCE LISTING AS A TEXT FILE

The Sequence Listing written in file 101285-000110PC_SequenceListing.txt created on Nov. 9, 2017, 28,672 bytes, machine format IBM-PC, MS-Windows operating system, is hereby incorporated by reference in its entirety for all purposes.

BACKGROUND OF THE INVENTION

During the recent years more and more attention has been given to various gluten-related disorders. A number of diseases and conditions are encompassed by this umbrella term due to their common triggering agent, gluten. Some examples of gluten-related disorders include celiac disease (CD), non-celiac gluten sensitivity (NCGS), gluten ataxia, dermatitis herpetiformis (DH), and wheat allergy. "Gluten intolerance" and "gluten sensitivity" are sometimes used to generally refer to such disorders.

Gluten, derived from the Latin word glue, is a mixture of storage proteins termed prolamins that are found in wheat and related grains, including barley, rye, and their hybrids. A substance that gives elasticity to dough helping it rise, keeping its shape, and often giving the final product a chewy texture, gluten is found in many staple foods made with wheat flour in the Western diet as well as in imitation meats in the Orient diet. Gliadins and glutenins are the two main components of gluten: gliadins are water-insoluble, but are soluble in 60% ethanol-water mixture, while glutenins occur as multimeric aggregates of large-molecular weight subunits. There are three main types of gliadin, α, γ, and ω, to which the body is intolerant in gluten-related disorders such as celiac disease.

Given the prevalence of gluten intolerance or gluten sensitivity, there exists an urgent need for effective methods and tools that allow individuals to conveniently test their food for fast and reliable detection of gluten in the food. The present invention fulfills this and other related needs.

BRIEF SUMMARY OF THE INVENTION

The present invention provides antibodies and antibody fragments that specifically bind to gliadin. Accordingly, in one aspect, the invention provides an isolated antibody or antibody fragment or a polypeptide comprising the antibody or fragment that binds to wheat gliadin as well as other related prolamin glycoproteins such as hordein (barley) and secalin (rye) at a newly defined and previously unknown epitope. In some embodiments, the epitope is an amino acid sequence comprising SEQ ID NO:21, such as an amino acid sequence no longer than 8, 9, or 10 amino acids (for instance, 6, 7, or 8 amino acids) in length, e.g., represented by the amino acid sequence set forth in any one of SEQ ID NOs:21-31, especially SEQ ID NO:22, or any one of SEQ ID NOs:23, 25-28, and 30-31. In one embodiments, the antibody, termed 13F6, comprises a heavy chain variable domain ($V_H$) having the amino acid sequence of SEQ ID NO:2 (which may be encoded by polynucleotide sequence of SEQ ID NO:1) and a light chain variable domain ($V_L$) having the amino acid sequence of SEQ ID NO:7 (which may be encoded by polynucleotide sequence of SEQ ID NO:6). More specifically, the $V_H$ amino acid sequence comprises a CDR1 of SEQ ID NO:3, a CDR2 of SEQ ID NO:4 and a CDR3 of SEQ ID NO:5, and $V_L$ amino acid sequence comprises a CDR1 of SEQ ID NO:8, a CDR2 of SEQ ID NO:9 and a CDR3 of SEQ ID NO:10.

In a related aspect, the invention provides an isolated antibody or antibody fragment that binds to gliadin. In some embodiments, the antibody, termed 14G11, comprises a heavy chain variable domain ($V_H$) having the amino acid sequence of SEQ ID NO:12 (which may be encoded by polynucleotide sequence of SEQ ID NO:11) and a light chain variable domain ($V_L$) having the amino acid sequence of SEQ ID NO:17 (which may be encoded by polynucleotide sequence of SEQ ID NO:16). More specifically, the $V_H$ amino acid sequence comprises a CDR1 of SEQ ID NO:13, a CDR2 of SEQ ID NO:14 and a CDR3 of SEQ ID NO:15, and $V_L$ amino acid sequence comprises a CDR1 of SEQ ID NO:18, a CDR2 of SEQ ID NO:19 and a CDR3 of SEQ ID NO:20.

With respect to embodiments of the 13F6 antibody, in some embodiments, the heavy chain variable domain has at least 90%, 93%, 95%, 97%, or 99% sequence identity to SEQ ID NO:2. In some embodiments, the light chain variable domain has at least 90%, 93%, 95%, 97%, or 99% sequence identity to SEQ ID NO:7. Generally, amino acid substitutions, additions and deletions are particularly tolerated within framework regions as described herein and identified in the amino acid and nucleic acid sequences of the 13F6 antibody. In some embodiments, the 13F6 antibody heavy and light chain variable regions have the amino acid sequence of SEQ ID NOs:2 and 7, respectively.

With respect to embodiments of the 14G11 antibody, in some embodiments, the heavy chain variable domain has at least 90%, 93%, 95%, 97%, or 99% sequence identity to SEQ ID NO:12. In some embodiments, the light chain variable domain has at least 90%, 93%, 95%, 97%, or 99% sequence identity to SEQ ID NO:17. Generally, amino acid substitutions, additions and deletions are particularly tolerated within framework regions as described herein and identified in the amino acid and nucleic acid sequences of the 14G11 antibody. In some embodiments, the 14G11 antibody heavy and light chain variable regions have the amino acid sequence of SEQ ID NOs:12 and 17, respectively.

The antibody or antibody fragment or a polypeptide comprising the antibody or fragment of this invention specifically bind to a gliadin or other associated prolamin glycoproteins such as wheat gliadin, barley hordein, or rye secalin. Some exemplary GenBank Accession Nos. include AJ133612.1, A27319 (wheat gliadin); 1210226A, AAA92333.1 (barley hordein); and AAG34498.1, ABO32294.1 (rye secalin).

In some embodiments, the antibody is an intact immunoglobulin, for example, an IgG or an IgM. In some embodiments, the antibody is a rodent or rabbit isotype IgG1. In some embodiments, the antibody is an antibody fragment, e.g., an scFv, a dsFv, a diabody, a domain antibody, a Fab or a F(ab')2, optionally fused to at least one (one or two, for example) peptide sequences of heterologous source(s). In some embodiments, the antibody or antibody fragment is chimeric or recombinantly produced to include sequences from two heterologous sources.

In some embodiments, the antibodies of the invention bind gliadin with a binding affinity ($K_D$) of about 100 nM or less, for example in the range of about 1-100 nM or about 5-50 nM or about 5-40 nM, for example, about 100 nM, 75 nM, 50 nM, 25 nM, 10 nM, 5 nM, 3 nM, 2 nM, 1 nM, or less. As shown in the examples, the 14G11 antibody has a $K_D$ less than 50 nM, typically about 30 nM; the 13F6 antibody has a $K_D$ of less than 10 nM, typically about 5-6 nM.

In some embodiments, the antibody, antibody fragment, or a polypeptide comprising the antibody or fragment, is linked to a heterologous moiety derived from a different source, i.e., not naturally found together with the antibody or fragment or the polypeptide. For example, the moiety may be one that facilitates detection, e.g., a radioisotope, an enzyme (especially one that can generate a colorimetrically measurable product), a fluorescent or chemiluminescent molecule.

In some embodiments, the heavy chain ($V_H$) and light chain ($V_L$) variable regions of the antibodies of the invention are joined by a peptide linker. In some embodiments, the $V_H$ and $V_L$ chains are connected by a disulfide bond between a cysteine residue engineered into each chain.

In a further aspect, the invention provides compositions comprising an antibody, a gliadin-binding fragment of the antibody, or a polypeptide comprising the antibody or fragment of the invention, and a pharmaceutically acceptable carrier. In some embodiments, the antibody is part of an immunoconjugate or a chimeric molecule. In some embodiments, the chimeric molecule includes a detectable moiety, which may be linked to the antibody or antibody fragment via a covalent linkage or a non-covalent linkage such as by physical adsorption.

The invention further provides isolated nucleic acids encoding the antibodies, gliadin-binding fragments, and polypeptides comprising the antibodies or fragments. With respect to an 13F6 antibody or antibody fragment, the nucleic acid encodes a heavy chain variable domain comprising a CDR1 of SEQ ID NO:3, a CDR2 of SEQ ID NO:4, and a CDR3 of SEQ ID NO:5. Alternatively, with regard to a 14G11 antibody, the nucleic acid encodes a heavy chain variable domain comprising a CDR1 of SEQ ID NO:13, a CDR2 of SEQ ID NO:14, and a CDR3 of SEQ ID NO:15. The same or a second nucleic acid encodes alight chain variable domain comprising a CDR1 of SEQ ID NO:8, a CDR2 of SEQ ID NO:9, and a CDR3 of SEQ ID NO:10 for the 13F6 antibody. Alternatively, the same or a second nucleic acid encodes a light chain variable domain comprising a CDR1 of SEQ ID NO:18, a CDR2 of SEQ ID NO:19, and a CDR3 of SEQ ID NO:20 for the 14G11 antibody. With respect to embodiments of the nucleic acids encoding a 13F6 antibody or antibody fragment, in some embodiments, the nucleic acid encodes a heavy chain variable domain sharing at least 90%, 93%, 95%, 97% or 99% sequence identity to SEQ ID NO:1. In some embodiments, the nucleic acid encodes a light chain variable domain sharing at least 90%, 93%, 95%, 97% or 99% sequence identity to SEQ ID NO:6. In some embodiments, the nucleic acid encoding a 14G11 heavy chain variable domain has at least 90%, 93%, 95%, 97% or 99% sequence identity with SEQ ID NO:11. In some embodiments, the nucleic acid encoding a 14G11 light chain variable domain has at least 90%, 93%, 95%, 97% or 99% sequence identity with SEQ ID NO:16.

In the embodiments of the 13F6 antibody, the nucleic acids encode $V_H$ and $V_L$ chains having the amino acid sequence of SEQ ID NOs:2 and 7, respectively. For example, the coding sequences may be SEQ ID NOs:1 and 6, respectively. In the embodiment of the 14G11 antibody, the nucleic acids encode $V_H$ and $V_L$ chains having the amino acid sequence of SEQ ID NOs:12 and 17, respectively. For example, the coding sequences may be SEQ ID NOs:11 and 16, respectively. Generally, nucleic acid substitutions, additions, and deletions are particularly tolerated within framework regions as described herein and identified in the nucleic acid sequences of the 13F6 and 14G11 antibodies in the Figures.

With respect to the 13F6 antibody or antibody fragment, the nucleic acid encodes a heavy chain variable domain comprising a CDR1 of SEQ ID NO:3, a CDR2 of SEQ ID NO:4, and a CDR3 of SEQ ID NO:5. The same or a second nucleic acid encodes a light chain variable domain comprising a CDR1 of SEQ ID NO:8, a CDR2 of SEQ ID NO:9, and a CDR3 of SEQ ID NO:10. With respect to embodiments of the nucleic acids encoding the 13F6 antibody or antibody fragment, in some embodiments, the nucleic acid encodes a heavy chain sharing at least 90%, 93%, 95%, 97% or 99% sequence identity to SEQ ID NO:2, with the nucleic acid itself having at least 90%, 93%, 95%, 97% or 99% sequence identity to SEQ ID NO:1. In some embodiments, the nucleic acid encodes a light chain sharing at least 90%, 93%, 95%, 97% or 99% sequence identity to SEQ ID NO:7, with the nucleic acid itself having at least 90%, 93%, 95%, 97% or 99% sequence identity to SEQ ID NO:6.

With respect to the 14G11 antibody or antibody fragment, the nucleic acid encodes a heavy chain variable domain comprising a CDR1 of SEQ ID NO:13, a CDR2 of SEQ ID NO:14, and a CDR3 of SEQ ID NO:15. The same or a second nucleic acid encodes a light chain variable domain comprising a CDR1 of SEQ ID NO:18, a CDR2 of SEQ ID NO:19, and a CDR3 of SEQ ID NO:20. With respect to embodiments of the nucleic acids encoding the 14G11 antibody or antibody fragment, in some embodiments, the nucleic acid encodes a heavy chain sharing at least 90%, 93%, 95%, 97% or 99% sequence identity to SEQ ID NO:12, with the nucleic acid itself having at least 90%, 93%, 95%, 97% or 99% sequence identity to SEQ ID NO:11. In some embodiments, the nucleic acid encodes a light chain sharing at least 90%, 93%, 95%, 97% or 99% sequence identity to SEQ ID NO:17, with the nucleic acid itself having at least 90%, 93%, 95%, 97% or 99% sequence identity to SEQ ID NO:16.

In another aspect, the invention provides any of the nucleic acids encoding the present antibodies, as described herein, operably linked to a promoter, especially a heterologous promoter that cannot be found in nature connected to the polynucleotide coding sequence(s) in the same manner. The invention further provides expression cassettes comprising the polynucleotide sequences encoding the anti-gliadin antibodies, gliadin-binding fragments, or polypeptides comprising the antibodies or fragments of the present invention. In some embodiments the expression cassettes are in the form of expression vectors. The invention further provides host cells comprising the nucleic acids or expression cassettes or expression vectors of the present invention.

In another aspect, the invention provides methods for detecting the presence of gliadin in a sample. The methods comprise contacting sample with an antibody of the invention. In some embodiments, the antibody is labeled, e.g., with a fluorescent, enzymatic or radioactive moiety. In some embodiments, the antibody has a constant region, e.g., IgG, IgM, IgA, that is conveniently detected with a labeled secondary antibody. The embodiments of the antibodies are as described herein.

In yet another aspect, the invention provides kits, e.g., for detecting the presence of a gliadin in a sample such as a food or beverage sample. The kits comprise one or more antibodies of the invention. The kits can also comprise a container and instructions for use of the one or more antibodies. In some embodiments, the antibodies are labeled or are in the form of an immunoconjugate. The embodiments of the antibodies are as described herein. In some embodiments, the kits further comprise a secondary antibody and/or a detectable label.

Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. gliadin The term "gliadin," as used in this application, generically refers to a protein commonly found in wheat products as well as other related prolamin glycoproteins such as hordein (barley) and secalin (rye). Amino acid sequences of gliadin are set forth in, for example, AJ133612.1, A27319 (wheat gliadin); 1210226A, AAA92333.1 (barley hordein); and AAG34498.1, ABO32294.1 (rye secalin).

"Antibodies" exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH—CH by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, W. E. Paul, ed., Fundamental Immunology, Raven Press, N.Y. (1993), for a more detailed description of these and other antibody fragments). While various antibody fragments are defined in terms of the digestion of an intact antibody, one of skill will appreciate that such Fab' fragments may be synthesized de novo either chemically or by utilizing recombinant DNA methodology.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. IgG$_1$, IgG$_2$, IgG$_3$ or IgG$_4$), IgD, IgA or IgE). In some embodiments, the antibody is an isotype human IgG1, for example, an isotype human IgGγ1.

The term "antibody fragments" means molecules that comprise a portion of an intact antibody, generally the antigen binding or variable region of the intact antibody. Examples of antibody fragments include Fab, Fab', F(ab')2, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11):484-490 (2003), Ghahroudi et al., FEBS Lett. 414:521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

As used herein, the term "anti-gliadin" in reference to an antibody, includes reference to an antibody which is generated against gliadin. The gliadin generally is a wheat gliadin.

The term "diabodies" refers to small antibody fragments with two antigen-binding sites, which fragments comprise a variable heavy domain ("V$_H$" or "VH") connected to a variable light domain ("V$_L$" or "VL") in the same polypeptide chain (V$_H$—V$_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Holliger et al., Proc. Natl. Acad. Sci. USA, 90: 6444-6448 (1993).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found.

References to "VH" or a "V$_H$" refer to the variable region of an immunoglobulin heavy chain, including an Fv, scFv, dAb, dsFv or Fab. References to "VL" or a "V$_L$" refer to the variable region of an immunoglobulin light chain, including of an Fv, scFv, dsFv, dAb, or Fab.

The term "Fv" refers to the variable domains of the heavy chain and of the light chain of an antibody. The phrase "single chain Fv" or "scFv" refers to an antibody in which the variable domains of the heavy chain and of the light chain of a traditional two chain antibody have been joined to form one chain. Optionally, a linker (usually a peptide) is inserted between the two chains to allow for proper folding and creation of an active binding site. If a linker is present, it is excluded for purposes of comparing the percentage of sequence identity between a given VH or VL chain and a VH or VL chain of the HN1 or the HN2 antibodies.

An antibody immunologically reactive with a particular antigen can be generated by recombinant methods such as selection of libraries of recombinant antibodies in phage or similar vectors, see, e.g., Huse, et al., *Science* 246:1275-

1281 (1989); Ward, et al., *Nature* 341:544-546 (1989); and Vaughan, et al., *Nature Biotech.* 14:309-314 (1996), or by immunizing an animal with the antigen or with DNA encoding the antigen.

The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The antibodies of the present invention can be encoded by nucleic acid sequences that correspond to a human germline sequence. The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other evaluated variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment, or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The term "linker peptide" includes reference to a peptide within an antibody binding fragment (e.g., Fv fragment) which serves to indirectly bond the variable domain of the heavy chain to the variable domain of the light chain.

A "detectable label" means, with respect to an immunoconjugate, a portion of the immunoconjugate that has a property rendering its presence detectable. For example, the immunoconjugate may be labeled with a radioactive isotope, which permits samples in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The terms "chimeric molecule" and "immunoconjugate" refer to linkage of an antibody to an effector moiety. The linkage is usually a covalent bond between the effector moiety and the antibody. The linkage can be by chemical conjugation, or by expressing the antibody and the effector moiety from a nucleic acid encoding both the antibody and the effector moiety. For example, a nucleic acid encoding an 14G11 or 13F6 antibody of the invention fused to an enzyme can be recombinantly expressed in *E. coli* and then isolated.

The term "connected to," in relation to an antibody and detectable label, means that the antibody is fused to (e.g., by recombinant expression) or conjugated to (e.g., chemically attached to) the detectable label, directly or through a linker.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W. H. Freeman and Company, New York (2nd Ed., 1992).

The terms "substantially similar" in the context of a peptide indicates that a peptide comprises a sequence with at least 90%, for example at least 95%, sequence identity to the reference sequence (e.g., SEQ ID NOs:2 and 7 or SEQ ID NOs:12 and 17) over a comparison window of at least 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, for example at least 80%, or at least 90-95% nucleotide or amino acid residue identity, when compared and aligned for maximum correspondence, as measured using one of the following sequence comparison algorithms or by visual inspection. The substantial identity can exist over a region of the sequences that is at least about 50 residues in length, for example, over a region of at least about 100 residues, or over at least about 150 residues. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on the internet by entering "www." followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (e.g., SEQ ID NOs:1 and 6 or SEQ ID NOs:11 and 16) if the smallest sum probability in a comparison of the test nucleic acid to the reference nucleic acid is less than about 0.1, for example less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The term "selectively reactive" or "specifically binds" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, for example greater than 5-fold, or greater than 10-fold and can result in greater than 100-fold increase in amount of bound antibody (per unit time) to a cell or tissue bearing gliadin as compared to a cell or tissue lacking gliadin. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods of the present invention are generally "physiological conditions" which include reference to conditions (e.g., temperature, osmolarity, pH) that are typical inside a living mammal or a mammalian cell.

While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Compositions or methods "comprising" one or more recited elements may include other elements not specifically recited. For example, a composition that comprises the VH and VL CDR sequences of the invention encompasses both the CDRs and the variable regions, antibodies and antibody fragments comprising the CDRs.

Compositions or methods "consisting essentially of" one or more recited elements include the elements specifically recited and may further include pharmacologically inactive components (e.g., excipients, vehicles), but do not include unrecited pharmacologically active agents.

The term "about," as used herein, describes a range of plus or minus 10% from a recited value. For example, a value of "about 10" can be any value within the range of 10±1, i.e., between 9 to 11.

BRIEF DESCRIPTION OF THE DRAWINGS

FIG. 1: The DNA and amino acid sequences of the heavy and light chain variable regions of antibody 13F6 (SEQ ID NOS:34-37, respectively).

FIG. 2: The DNA and amino acid sequences of the heavy and light chain variable regions of antibody 14G11 (SEQ ID NOS:38-41, respectively).

FIG. 4: Indirect ELISA results from antibodies 13F6 (a) and 14G11 (b) as well as the commercial R5 (c) antibody against wheat, barley, rye, oat, and 33-mer. All antigens were coated overnight at 20 μg/ml, 100 μl in each well. After standard blocking and washing procedures, antibodies was added at 0.8-20 ng/ml, in 100 μl, and incubated at 25° C. for 1 hour. After washing steps, anti-mouse HRP was added and plates were incubated for 1 hour, followed by TMB (peroxidase substrate) addition and further incubation for 5 minutes. After acid quenching, absorbance was measured at 450 nm.

DETAILED DESCRIPTION

I. Anti-Gliadin Antibodies

Figure 3:
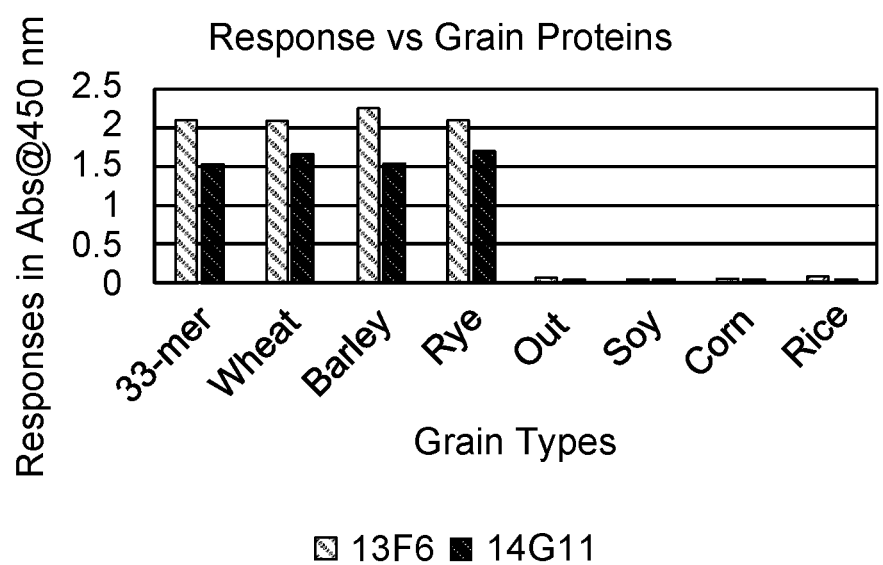
FIG. 3: Indirect ELISA results from 13F6 and 14G11 clones against gluten and non-gluten proteins. All antigens were coated overnight at 1 μg/ml, 100 μl in each well. After standard blocking and washing procedures, antibodies were added at 10 ng/ml, in 100 μl, and plates incubated at 25° C. for 1 hour. After washing steps, anti-mouse HRP were added and incubated for 1 hour, followed by TMB addition for 6 minutes. After acid quenching, absorbance was measured at 450 nm.
Figure 5:
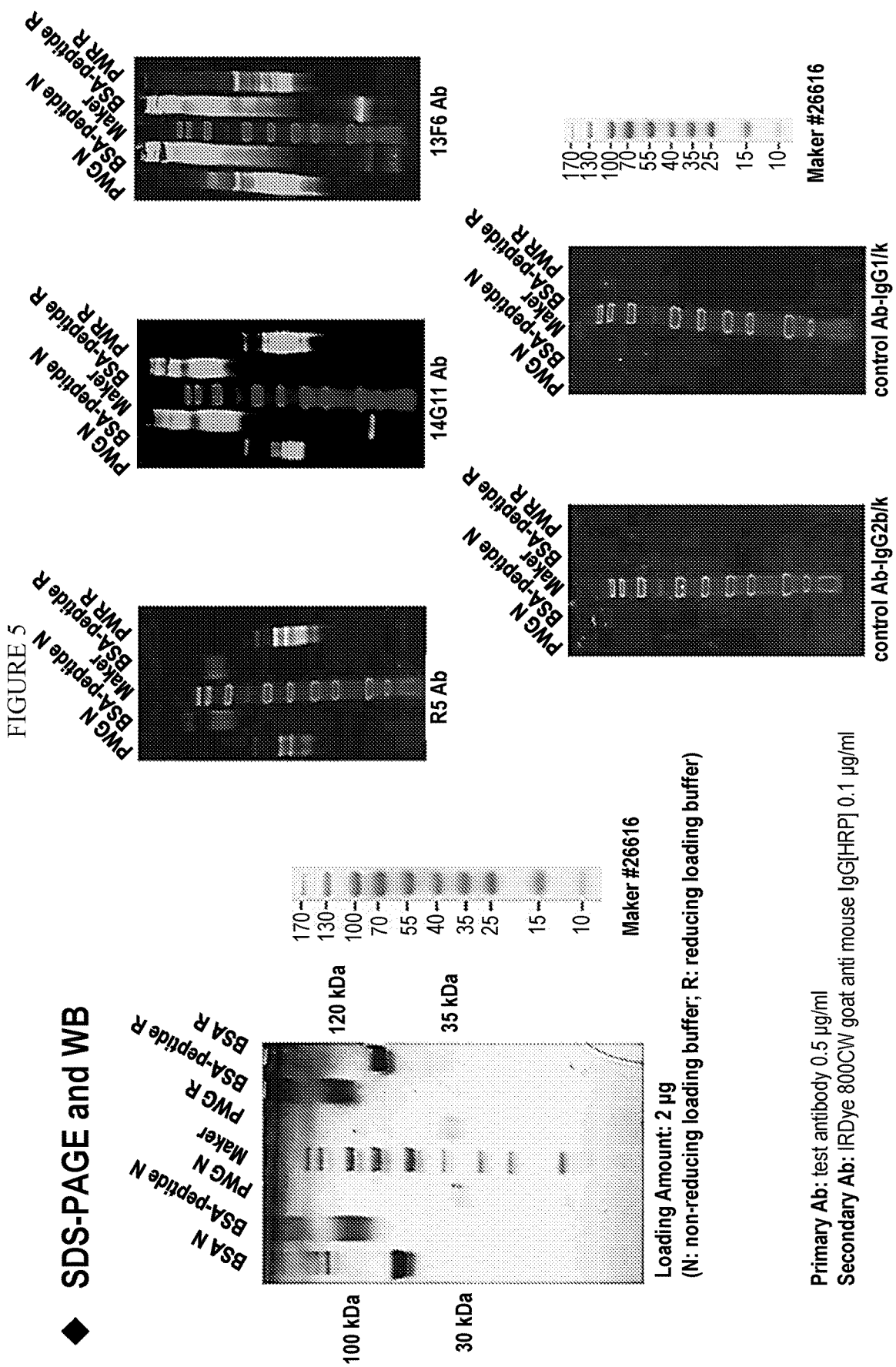
FIG. 5: SDS-Page and Western Blot data for R5, 14G11, 13F6, IgG2b and IgG1 control against 33-mer conjugated BSA, and PWG gliadins.

Due to the significant rise in the instances of gluten-intolerance during the recent years, there is a corresponding increased need for developing a rapid and reliable means of detecting the presence of gluten in food or beverage so as to permit individuals having gluten-sensitivity to determine, in a real-world sense, their food or drink choices. The present invention provides novel anti-gliadin antibodies that can be used in a kit and method for rapid detection of gluten with high sensitivity and accuracy.

In some embodiments, the present invention provides anti-gliadin antibodies that recognize a previously undefined epitope of gliadin. This newly defined epitope is an amino acid sequence comprising SEQ ID NO:21, for example, represented by the amino acid sequence set forth in any one of SEQ ID NOs:22-29. In some examples, the antibody includes CDRs 1, 2, and 3 of the $V_H$ region (i.e., SEQ ID NOs:3, 4, 5, and 2, respectively) and CDRs 1, 2, and 3 of the $V_L$ region (i.e., SEQ ID NOs:8, 9, 10, and 7, respectively) of the 13F6 antibody as those CDRs are shown in FIG. 1. In some embodiments, the invention provides anti-gliadin antibodies having CDRs 1, 2, and 3 of the $V_H$ region (i.e., SEQ ID NOs:13, 14, 15, and 12, respectively) and CDRs 1, 2 and 3 of the $V_L$ region (i.e., SEQ ID NOs:18, 19, 20, and 17, respectively) of the 14G11 antibody as those CDRs are shown in FIG. 2.

While the exemplary antibodies, 13F6 and 14G11, have the amino acid sequence of heavy chain variable domains set forth in SEQ ID NO:2 and SEQ ID NO:12, respective, and the amino acid sequence of light chain variable domains set forth in SEQ ID NO:7 and SEQ ID NO:17, respectively, it is well known to those of skill in the art that the same antibody binding characteristics can be conserved by maintaining the same CDRs in the heavy and light chains while the framework regions is modified (e.g., humanized). Furthermore, single chain antibodies having essentially the same antigen-binding characteristics can be made by fusion of the matching $V_H$ and $V_L$ of an antibody (e.g., 13F6 or 14G11) without including some or all of the constant regions of the heavy and light chains. The exemplary DNA sequences encoding the heavy and light chains of the anti-gliadin antibodies are provided in FIGS. 1 and 2, however, alternative DNA coding sequences may be used to recombinantly produce the same antibodies due to codon-wobbling.

The anti-gliadin antibodies of the present invention not only recognize previously undefined gliadin epitope, an amino acid sequence no longer than 8-10 amino acids comprising SEQ ID NO:21 (e.g., the epitope having the amino acid sequence of any one of SEQ ID NO:22-31), they also exhibit surprisingly high level of antigen affinity compared to known gliadin antibodies such as R5, G12, and A1, etc. See, e.g., Osman et al., J. Gastroenterology & Hepatology 2001, 13:1189-1193; Moron et al., PLoS ONE 2008, 3(5): e2295, 1-13. Typically the anti-gliadin antibodies of the present invention exhibit a KD in binding with wheat gliadin less than about 200 nM, about 100 nM, or about 50 nM, for example, between about 1-100 nM, about 2-50 nM, about 4-50 nM, or about 5-50 nM.

II. Production of Immunoconjugates

The anti-gliadin antibodies of the invention can be linked to detectable molecules (DM) through the DM carboxyl terminus, the DM amino terminus, through an interior amino acid residue of the DM such as cysteine, or any combination thereof. Similarly, the DM can be linked directly to heavy, light, Fc (constant region) or framework regions of the antibody. Linkage can occur through the antibody's amino or carboxyl termini, or through an interior amino acid residue. Further, multiple DM molecules (e.g., any one of from 2-10) can be linked to the anti-gliadin antibody and/or multiple antibodies (e.g., any one of from 2-5) can be linked to an DM. The antibodies used in a multivalent immunoconjugate composition of the present invention can be directed to the same or different gliadin epitopes. In addition to a covalent linkage, a non-covalent linkage (e.g., via physical adsorption) can be used in making the immunoconjugate as well.

Immunoconjugates include, but are not limited to, molecules in which there is a detectable agent linked to an antibody via a covalent linkage or non-covalent linkage (e.g., by way of physical adsorption). A detectable agent is an agent having the capability of generating a detectable signal, e.g., radioactive, colormetric, fluorescent, time-resolved fluorescence, luminescence, electrical, electrochemical, or electromagnetic signal.

A. Recombinant Methods

The nucleic acid sequence encoding a immunoconjugate comprising the anti-gliadin antibody of the present invention and a detectable moiety can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (3RD ED.), Vols. 1-3, Cold Spring Harbor Laboratory (2001)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987-2009). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding an anti-gliadin antibody or binding fragment thereof or the detectable molecule (DM) can be modified to form the immunoconjugates of the present invention. Modification by site-directed mutagenesis is well known in the art. Nucleic acids encoding DM or anti-gliadin antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes an anti-gliadin scFv antibody into a vector which comprises the cDNA encoding the DM. The insertion is made so that the scFv and the DM are read in frame, that is in one continuous polypeptide containing a functional Fv region and a functional DM region.

Once the nucleic acids encoding a DM, anti-gliadin antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-gliadin antibody an immunoconjugate formed from the combination of the antibody and a DM) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates, DM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

B. Purification

Once expressed, the recombinant immunoconjugates, antibodies, and/or detectable molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for diagnostic uses.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

C. Detectable Labels

In some embodiments, the antibodies of the invention or a binding fragment thereof or a polypeptide comprising the antibody or fragment can be coupled to detectable labels. The linkage can be covalent or non-covalent. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$I, $^{14}$C, or $^{32}$P) enzymes (e.g., horse radish peroxidase, alkaline phosphatase and others commonly used in an ELISA), and colorimetric labels such as colloidal gold or colored glass or plastic (e.g. polystyrene, polypropylene, latex) beads.

Means of detecting such labels are well known to those of skill in the art. Thus, for example, radiolabels may be detected using photographic film or scintillation counters, fluorescent markers may be detected using a photodetector to detect emitted illumination.

Enzymatic labels are typically detected by providing the enzyme with a substrate and detecting the reaction product produced by the action of the enzyme on the substrate, and colorimetric labels are detected by simply visualizing the colored label.

D. Conjugation to the Antibody

In a non-recombinant embodiment of the invention, detectable molecules are linked to the anti-gliadin antibodies of the present invention using any number of means known to those of skill in the art. Both covalent and noncovalent attachment means may be used with anti-gliadin antibodies of the present invention.

The procedure for attaching an effector molecule to an antibody will vary according to the chemical structure of the DM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules, such as those available from Pierce Chemical Company (Rockford Ill.).

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the detectable molecule are polypeptides, the linkers may be joined to the constituent amino acids through their side groups (e.g., through a disulfide linkage to cysteine). In some embodiments, the linkers may be joined to the alpha carbon amino and carboxyl groups of the terminal amino acids.

In view of the large number of methods that have been reported for attaching a variety of fluorescent/chemiluminescent compounds, enzymes, dyes, and other agents (e.g., latex particles, nanoparticles, naoncrystals, colloidal gold, etc.) to antibodies one skilled in the art will be able to determine a suitable method for attaching a given agent to an antibody or other polypeptide.

III. Kits and Uses

In another embodiment, this invention provides for kits for the detection of gliadin or an immunoreactive fragment thereof, (i.e., collectively, a "gliadin protein") in a food or beverage sample. A "food or beverage sample" as used herein is a sample of any substance intended for human consumption in the form of solid, semi-solid, or liquid that potentially could contain gliadin.

Kits will typically comprise an anti-gliadin antibody or antibody fragment of the present invention, the embodiments being as described herein. In some embodiments, the anti-gliadin antibody or antibody fragment will be an anti-gliadin Fv fragment, such as a scFv fragment, or a recombinant polypeptide comprising an anti-gliadin antibody or a gliadin-binding fragment thereof plus a heterologous amino acid sequence.

In addition the kits will typically include instructional materials disclosing means of use of an antibody of the present invention (e.g. for detection of gliadin in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. In some cases, a positive control (a gliadin-containing sample) may be included in the kit to ensure that that detection assay is operating correctly. Such kits and appropriate contents are well known to those of skill in the art.

In one embodiment of the present invention, the gliadin-detection kit comprises an immunoassay. As described above, although the details of the immunoassays of the present invention may vary with the particular format employed, the method of detecting gliadin in a food or beverage sample generally comprises the steps of contacting the sample with an antibody that specifically reacts, under immunologically reactive conditions, to gliadin. The antibody is allowed to bind to gliadin under immunologically reactive conditions, and the presence of the bound antibody is detected directly or indirectly. The anti-gliadin antibody may be used, for example, as the capture antibody of an ELISA, or as a second antibody to bind to gliadin captured by the capture antibody. In some embodiments, the kits comprise an antibody or antibody fragment pre-bound to a solid support, e.g., a microchip, a microtiter plate or a bead. As is known in the art, the presence of the second antibody is typically then detected.

The antibodies provided herein are useful as diagnostic agents and in in vitro assays to detect the presence of gliadin in test samples. For example, the antibodies 13F6 and 14G11 and variants of these antibodies as described herein can be used as the targeting moieties of immunoconjugates in immunohistochemical assays to determine whether a sample contains gliadin. If the sample is one taken from a food item that is in solid form, processing steps of grinding and mixing/solubilizing may be necessary before the immunoassay can be conducted. As such, the kit optionally contains a solution suitable for dissolving the ground food sample before an immunoassay can be performed, see, e.g., U.S. patent application Ser. No. 15/065,198, U.S. Patent Application Publication No. US20140295406A1.

EXAMPLES

The following examples are provided byway of illustration only and not byway of limitation. Those of skill in the art will readily recognize a variety of non-critical parameters that could be changed or modified to yield essentially the same or similar results.

Example 1: Production and Functional Analysis of 13F6 and 14G11

Two clones of anti-gliadin antibodies, 13F6 and 14G11, have been identified as exhibiting high and comparable responses to barley, wheat, rye and a 33-mer amino acid sequence derived from the wheat gliadin protein (SEQ ID NO:33) (see, e.g., Shan et al., *Science* 297:2275-2279, 2002; Moron et al., *PLoS ONE*, 3(5):e2994:1-13, 2008; Moron et al., *Am. J. Clin. Nutr.* 87:405-414, 2008). 13F6 is an IgG2b antibody, whereas 14G11 is an IgG1 antibody.

Monoclonal antibodies 14G11 and 13F6 were raised by immunizing five (5) 8-9 week old female BALB/c mice with a 33-mer gluten specific peptide (amino acid sequence LQLQPFPQPQLPYPQPQLPYPQPQLPYPQPQPF (SEQ ID NO:33), Shan et al., Science 297:2275-2279, 2002) conjugated to KHL (Keyhole limpet hemocyanin), as well as gluten prolamins using standard immunization procedure. Serum samples obtained from blood draws were used to monitor titers of target specific antibodies in animals by indirect ELISA using wheat, barley, rye prolamins and unconjugated gluten specific peptide. Two animals with the highest serum titers were given the final immunization with 10 µg of gluten specific peptide in PBS intravenously three days before spleen harvest. Spleens of these mice were removed, spleen cells were extracted and fused with P3X63Ag8.653 mouse myeloma cells (ATCC, CRL-1580). Hybridoma cells were generated following standard protocols. Then hybridoma supernatants were collected and screened by indirect ELISA for the reactivity against gluten specific immunogenic peptide, barley, wheat, rye, oat, rice, corn and soy proteins. Purified antibodies were produced in protein A chromatography.

Specifically, both 13F6 and 14G11 show comparable responses to wheat, barley and rye proteins, but do not respond to other non-gluten grains, especially oat (FIGS. 3 and 4). This is highly desirable because oat, while similar to gluten, is not actually a gluten protein. Some other commercial assays (Romer Labs, or GlutenTox) use antibodies such as G12 and A1(Morón, B., Á. Cebolla, H. Manyani, M. Álvarez-Maqueda, M. Megias, M. del Carmen Thomas, M. C. López, and C. Sousa, *Sensitive detection of cereal fractions that are toxic to celiac disease patients by using monoclonal antibodies to a main immunogenic wheat peptide*. The American journal of clinical nutrition, 2008. 87(2): p. 405-414), which cross-react with oat and are therefore not ideal for gluten detection. In addition, 13F6 and 14G11 are much more sensitive to all gluten types than the well-accepted gold standard, the R5 antibody (Hernando, A., J. R. Mujico, D. Juanas, and E. Méndez, *Confirmation of the Cereal Type in Oat Products Highly Contaminated with Gluten*. Journal of the American Dietetic Association, 2006. 106(5): p. 665; Kahlenberg, F., D. Sanchez, I. Lachmann, L. Tuckova, H. Tlaskalova, E. Méndez, and T. Mothes, *Monoclonal antibody R5 for detection of putatively coeliac-toxic gliadin peptides*. European Food Research and Technology, 2006. 222(1-2): p. 78-82) (FIG. 4C). R5 is obtained from the Spanish National Center for Biology via Operon (website: operon.es).

TABLE 1

Binding characteristics of 13F6 and 14G11 in comparison with R5

| [Ab], ng/ml | Wheat 13F6 | | Wheat 14G11 | | Wheat R5 | | Barley 13F6 | | Barley 14G11 | | Barley R5 | | Rye 13F6 | | Rye 14G11 | | Rye R5 | |
|---|---|---|---|---|---|---|---|---|---|---|---|---|---|---|---|---|---|---|
| 20 | 2.574 | 2.568 | 2.252 | 2.25 | 1.496 | 1.521 | 2.4 | 2.41 | 2.037 | 2.007 | 1.617 | 1.609 | 2.184 | 2.188 | 1.843 | 1.896 | 1.56 | 1.611 |
| 4 | 1.548 | 1.542 | 1.202 | 1.207 | 0.534 | 0.534 | 1.494 | 1.473 | 1.097 | 1.083 | 0.63 | 0.659 | 1.254 | 1.288 | 0.854 | 0.881 | 0.651 | 0.671 |
| 0.8 | 0.567 | 0.587 | 0.393 | 0.396 | 0.133 | 0.133 | 0.49 | 0.482 | 0.338 | 0.357 | 0.165 | 0.171 | 0.415 | 0.416 | 0.262 | 0.258 | 0.165 | 0.174 |
| 0 | 0.046 | 0.046 | 0.049 | 0.041 | 0.039 | 0.043 | 0.04 | 0.04 | 0.041 | 0.041 | 0.041 | 0.042 | 0.039 | 0.042 | 0.04 | 0.038 | 0.039 | 0.042 |

| [Ab], ng/ml | 33-Mer 13F6 | | 33-Mer 14G11 | | 33-Mer R5 | | Oat 13F6 | | Oat 14G11 | | Oat R5 | |
|---|---|---|---|---|---|---|---|---|---|---|---|---|
| 20 | 2.194 | 2.09 | 1.986 | 1.992 | 0.067 | 0.118 | 0.043 | 0.044 | 0.04 | 0.042 | 0.043 | 0.048 |
| 4 | 1.085 | 1.078 | 1.121 | 1.109 | 0.048 | 0.052 | 0.042 | 0.047 | 0.04 | 0.047 | 0.042 | 0.043 |
| 0.8 | 0.342 | 0.349 | 0.376 | 0.363 | 0.039 | 0.04 | 0.042 | 0.044 | 0.042 | 0.046 | 0.041 | 0.055 |
| 0 | 0.04 | 0.041 | 0.039 | 0.041 | 0.04 | 0.04 | 0.043 | 0.042 | 0.043 | 0.049 | 0.043 | 0.044 |

Antigens coating: Barley, Rye, Wheat, 33-mer, Oat, 1 ug/mL in 50 mM Carbonate buffer pH 9.4, 4° C., overnight.
Individual gliadins: Glaidin (PWG), 5 mg/mL, 60% EtOH, Barley and Rye (Aromalab.de), 5 mg/mL, 60% EtOH
Oat mixture, 4 ug/mL 60% EtOH. 1 mg/mL of each of four oats:
Oat1 Clav950,
Oat0 AV06ID,
Oat2, 168069,
Oat5, 168069,
Blocking: SEBB, 300 uL/well, RT, 1.5 hour
1st Ab (43G2, R5,13F6 and 14G11): 20-08 ng/mL in SEDB, 100 uL/well, RT, 1 hour
2nd Ab: goat anti-mouse IgG Fc (Jackson Lab Cat# 115-035-008) 160 ng/mL in SEDB, 100 uL/well, RT, 1 hour
TMB: RT, 5 minutes
Notes:
Desired response: wheat, barley, rye, 33mer. Undesired response: oat and others.

Example 2: Affinity Studies

1. Objective

The aim of the current study is to measure the binding affinities between glutenin and three monoclonal antibodies using Biacore T200.

2. Materials

Test articles are listed below in Table 2 below:

TABLE 2

| Samples | MW (kDa) | Concentration (mg/ml) |
|---|---|---|
| Gluten | Obtained from PWG group. It is a gluten mixture. ** Based on MS, 31.7 kDa was used to calculate molar concentration | 10 |
| 14G11 | ~140 kDa estimated from SDS-PAGE | 4.94 |
| 13F6 | | 5.2 |
| R5 | | 8 |

** PWG-gliadin is a reference material that has been produced under the guidance of the Prolamin Working Group (PWG). Its isolation and characterization is described in detail in van Eckert et al. (2006). Briefly, PWG-gliadin has been extracted from a mixture of 28 European wheat cultivars. Albumins and globulins were eliminated by extraction using 0.4M NaCl solution and gliadins were extracted with 60% ethanol. The gliadin extracts were concentrated, desalted by ultrafiltration, freeze-dried, and homogenized. The residual material after lyophilization is referred to as PWG-gliadin.

Biacore T200 (GE Healthcare)
Series S Sensor Chip CM5 (GE Healthcare Cat. No. BR-1005-30 Lot No.: 10229292)
Capture antibody: Anti-mouse Fc gamma specific antibody, Cat. No. 115-005-071 (Jackson ImmunoResearch), 20 μg/ml in 10 mM Na-acetate pH 5.0
NHS: 100 mM N-hydroxysuccinimide in $H_2O$
EDC: 400 mM 1-ethyl-3-(3-dimethylaminopropyl) carbodiimide in $H_2O$
Ethanolamine: 1 M ethanolamine hydrochloride, adjusted to pH 8.5 with NaOH
Running buffer HBS-EP: 10 mM HEPES pH 7.4, 150 mM NaCl, 3 mM EDTA, 0.005% Tween-20
50 mM HCl
10 mM Glycine-HCl, pH 2.0
50 mM HCl, 3 M $MgCl_2$ 3. Experimental Procedures 3.1 Glutenin Immobilized Through Amine Coupling In this experiment, glutenin protein was coated through amine coupling method, the antibodies were flowed over the sensor chip as analytes. The experiment was carried out using the following protocol.

3.1.1 Covalent Coupling of Glutenin

Coat glutenin onto the Series S Sensor Chip CM5 via primary amine groups using the following conditions:
(1) Equilibrate: HBS-EP, flow rate 10 l/min, 5 min;
(2) Activate surface: inject NHS+EDC 1:1 mixture, flow rate 10 l/min, 7 min;
(3) Couple ligand: inject glutenin (15 μg/ml, 10 mM sodium acetate, pH 4.5), flow rate 10 l/min, until 300 RU of glutenin is coated;
(4) Deactivate excess reactive groups: inject ethanolamine, flow rate 10 l/min, 7 min.

3.1.2 Affinity Measurement

Test the pair-wise binding of test articles to the glutenin using the following assay setup:
(1) Stabilize surface: Perform three start-up cycles with a dummy sample (HBS-EP buffer);
(2) Equilibrate: flow running buffer over all flow cells for 1.5 hours;
(3) Associate: inject the antigen at the lowest concentrations (see Parameter Summary Table below) over all flow cells, flow rate 30 l/min, 14G11 and 13F6, 5 min and R5, 2.5 min;
(4) Dissociate: flow running buffer over all flow cells, flow rate 30 l/min, 14G11 and 13F6, 15 min and R5, 2.5 min;
(5) Regenerate surface: flow regeneration buffer (14G11 and 13F6, 10 mM Glycine-HCl and R5, 50 mM HCl, 3 M $MgCl_2$) 3 times, flow rate 100 l/min, 15 sec;

(6) Increase the analyte concentration by 2 or 3 fold, repeat steps (1) through (5). All together there were five analyte concentrations and one repeat of a medium concentration (see Parameter Summary Table 3 below). The curve of the repeat cycle should coincide with that of the previous cycle to confirm that the regeneration condition was appropriate.

TABLE 3

| Analyte | 14G11 | 13F6 | R5 |
|---|---|---|---|
| Immobilization | | | |
| Ligand | | Glutenin | |
| Immobilization level (RU) | | 283.8 | |
| Association and Dissociation | | | |
| Flow rate (μl/min) | | 30 | |
| Association time (s) | 300 | 300 | 150 |
| Dissociation time (s) | 600 | 600 | 150 |
| Sample Concentration | | | |
| Concentration (nM) | 3, 9, 27(×2), 81, 243 | 3, 9(×2), 27, 81, 243 | 20, 40, 80(×2), 160, 320 |
| Regeneration | | | |
| Flow rate (μl/min) | | 100 | |
| Regeneration contact time (s) | | 15(×3) | |
| Regeneration buffer | 10 mM Glycine-HCl | 10 mM Glycine-HCl | 50 mM HCl, 3M MgCl$_2$ |

4. Results and discussion

The experimental data were processed, and fitted locally to 1:1 interaction model in Biacore T200 evaluation software. The model describes interaction A+B=AB, is the simplest model for kinetic evaluation, therefore is recommended as default unless there is good reason to choose a different model.

Figure 6:
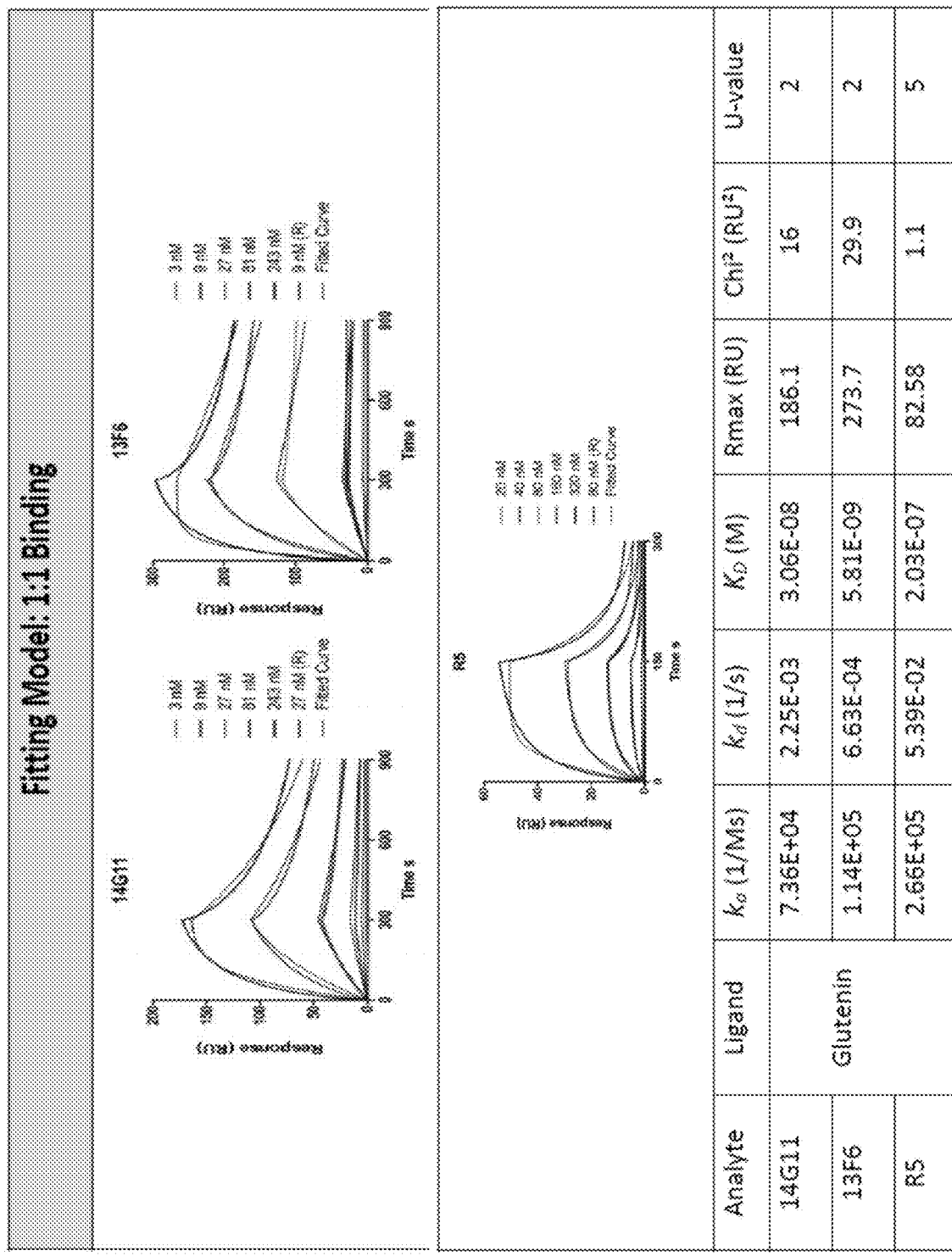
FIG. 6: Results of affinity measurement for 14G11 and 13F6 using Biacore T200 software. Fitting Model: 1:1 binding.

The experimental result is summarized in FIG. 6.

The curves of medium concentrations coincided, suggesting that the regeneration conditions were good. The gluten surface was not damaged after several cycles of regeneration. The Chi$^2$ were about or below 10% of the Rmax, which means that the fitting of experimental data to 1:1 interaction model was not perfect but reliable. The U-values of all three antibodies were low, ≤5. All in all, the curve fitting is good enough and the result is reliable. The result should better reflect the real binding affinity between gluten and antibodies.

5. Summary

In this study, the binding affinities between glutenin and three monoclonal antibodies were determined. The experiment was carried out where glutenin was amine coupled to the sensor chip and antibodies were used as analytes. The result of is with good curve fitting and low U-values, and thus is reliable.

Example 3: Binding Validation and Epitope Mapping

Materials
Antigen: Modified Gliadin(PWG)
  6SEN 33-Mer peptide Unconjugated, 33-mer peptide (5 mg/ml)
  6SEN 33-Mer peptide BSA-conjugated, BSA-33 mer peptide (5 mg/ml)
Antibody: R5 monoclonal Ab (8 mg/ml)
  14G11 monoclonal Ab (4.94 mg/ml)
  13F6 monoclonal Ab (5.2 mg/ml)

Other reagents and solutions:
  PBS buffer: NaCl 137 mM; KCl 2.7 mM; Na$_2$HPO$_4$ 4.3 mM; KH$_2$PO$_4$ 1.4 mM, pH 7.4
  PBS-T buffer: PBS buffer with 0.05% Tween 20
  Coating buffer: 0.05 M NaHCO$_3$, pH 9.6
  Blocking Buffer: PBS buffer with 5% skimmed milk
  TMB
  1 M HCl
  Goat anti-mouse IgG antibody(H+L)[HRP], GenScript
  IRDye800CW goat anti-mouse IgG (H+L), LI-COR

TABLE 5

| ELISA condition | |
|---|---|
| Ag Coating | BSA (negative ctrl)/BSA-Peptide/33-mer Peptide/Modified Gliadin (PWG) (targets) 10 μg/ml incubated at 4° C. overnight |
| Blocking | 5% MPBS, incubated at RT for 1.5 h |
| Primary Ab | diluted Ab 10x starting from 10 μg/ml in 0.05% PBST, incubated at 4° C. for 1.5 h |
| Secondary Ab | Goat anti-mouse IgG [HRP] 0.1 μg/ml, incubated at 4° C. for 45 min |
| Western blot condition | |
| Blocking | 5% MPBS, incubated at RT for 1 h |
| Primary Ab | diluted mAb 0.5 μg/ml in 0.05% PBST, incubated at RT for 1.5 h |
| Secondary Ab | IRDye 800CW goat anti mouse IgG [HRP] 0.1 μg/ml, incubated at RT for 45 min |

All three mAbs bound the target specifically.

The binding affinity of R5 is lower than the other two mAbs, which is consistent with the result of affinity measurement by Biacore.

Antigen1 is a protein of 296 amino acids.

```
                                          (SEQ ID NO: 42)
MKTFLILALL AIVATTATTA VRVPVPQPQP QNPSQPQPQR

QVPLVQQQQF PGQQQQFPPQ QPYPQPQPFP SQQPYLQLQP

FPQPQPFPPQ LPYPQPPPFS PQQPYPQPQP QYPQPQQPIS
```

```
                                       -continued
QQQAQQQQQQ QQQQQQQQQQ QQILPQILQQ QLIPCRDVVL

QQHNIAHARS QVLQQSTYQP LQQLCCQQLW QIPEQSRCQA

IHNVVHAIIL HQQQQQQQPS SQVSLQQPQQ QYPSGQGFFQ

PSQQNPQAQG SVQPQQLPQF EEIRNLALQT LPRMCNVYIP

PYCSTTTAPF GIFGTN
```

Antigen2 is a protein of 290 amino acids.

```
                                       (SEQ ID NO: 43)
MVRVPVPQLQ PQNPSQQQPQ EQVPLVQQQQ FPGQQQPFPP

QQPYPQPQPF PSQQPYLQLQ PFPQPQLPYP QPQLPYPQPQ

LPYPQPQPFR PQQPYPQSQP QYSQPQQPIS QQQQQQQQQQ

QQKQQQQQQQ QILQQILQQQ LIPCRDVVLQ QHSIAYGSSQ

VLQQSTYQLV QQLCCQQLWQ IPEQSRCQAI HNVVHAIILH

QQQQQQQQQQ QQPLSQVSFQ QPQQQYPSGQ GSFQPSQQNP

QAQGSVQPQQ LPQFEEIRNL ALETLPAMCN VYIPPYCTIA

PVGIFGTNYR
```

Antigen3 is a peptide of 33 amino acids.

```
                                       (SEQ ID NO: 33)
      LQLQPFPQPQ LPYPQPQLPY PQPQLPYPQP QPF
```

Peptide library design: peptide length/overlapping/offset=10aa/7aa/3aa; Cys was replaced by Ser in the peptide library; N-terminal biotinylated; crude product.

TABLE 6

| Epitope mapping screening-condition Epitope ELISA condition | | |
|---|---|---|
| Coating | Streptavidin (Anchor protein); 10 μg/ml incubated at 4° C. overnight | 33-Mer Peptide (positive Ctrl); Modified Gliadin(PWG) (positive Ctrl) 10 μg/ml incubated at 4° C. overnight |
| Blocking | 5% MPBS, incubated at RT for 1.5 h | |
| Capture | crude peptide 50 μg/ml each, incubated at RT for 1.5 h | / |
| Primary Ab | R5 2 μg/ml; 14G11, 13F6, IgG2b control mAb, IgG1 control mAb 0.5 μg/ml incubated at RT for 1.5 h, incubated at RT for 1.5 h | |
| Secondary Ab | Goat anti-mouse IgG [HRP] 0.1 μg/ml, incubated at RT for 45 min | |

All peptides designed from antigen 1/2/3 are available except 42, AQQQQQQQQQ (SEQ ID NO:44).

The binding between peptide libraries and mAbs were assayed by ELISA. And isotype and blank PBS control binding was included.

ELISA against peptide libraries was done twice. The result is the same. The binding between mAbs and peptide binders identified from the libraries was done once again to confirm the result.

13F6 and 14G11 seemed to recognize the same epitope. The ELISA OD450 values of 13F6 were slightly higher than those of 14G11, suggesting the binding affinity of 13F6 was slightly higher, which is consistent with the result of affinity measurement.

None of the peptides seemed to bind R5. Even at R5 concentration as high as 10 g/ml, none of antigen 3 peptides or 'QQPFP' (SEQ ID NO:45)—containing peptides bound R5 (data not show). The peptides used for this study were crude peptides with low purity, coupled with the fact that the binding affinity of R5 was extremely low, with KD of ~0.2 μM. This might result in this outcome.

Peptide 42 (AQQQQQQQQQ (SEQ ID NO:44)) is the only one peptide that is not available. Seeing that peptide 43 (QQQQQQQQQQ (SEQ ID NO:45)) did not bind any of the three mAbs and the sequence of peptide 42 is not similar to those of identified peptide binders, it is highly possible that the peptide would not bind the mAbs.

Based on the screening result, 13 peptides could be recognized by the 13F6 and 14G11 antibodies.

These 13 peptides all have a common amino acid sequence of 'Q(Q/L)PYPQ.' (SEQ ID NO:21) The stretch of Q(Q/L)PYPQ (SEQ ID NO:21) sequence is believed to be the core of epitopes of 13F6 and 14G11 antibodies. This is in contrast to epitope sequences of previously known anti-gliadin antibodies (A1: QLPYPQP (SEQ ID NO:26); R5: QQPFP (SEQ ID NO:45); G12: QPQLPY (SEQ ID NO:47); QPQQPY (SEQ ID NO:48); QPQLPF (SEQ ID NO:49)).

The OD450 values of group B were lower than those of group A, suggesting the C-terminal residue(s), e.g., P or PQ, contributed to antigen binding. See Table 7 below.

TABLE 7

| Group | OD450 nm | Common sequence | Peptides | | | | |
|---|---|---|---|---|---|---|---|
| A | ~2.0 (13F6) | Q(Q/L)PYPQ(P/S) (SEQ ID NO: 24) | PQQPYPQPQP (SEQ ID NO: 50) | PQPQLPYPQP (SEQ ID NO: 51) | QLPYPQPLP (SEQ ID NO: 52) | PQLPYPQPQP (SEQ ID NO: 53) | PPQQPYPQPQ (SEQ ID NO: 54) |
| | ~1.0 (14G11) | | SPQQPYPQPQ (SEQ ID NO: 55) | QPQLPYPQPQ (SEQ ID NO: 56) | PQLPYPQPQL (SEQ ID NO: 57) | PQQPYPQSQP (SEQ ID NO: 58) | PPQLPYPQPP (SEQ ID NO: 59) |
| B | >1 (13F6) >0.5 (14G11) | PQ(Q/L)PYPQ (SEQ ID NO: 29) | PFPPQQPYPQ NO: 60) | YPQPQLPYPQ NO: 61) | PFRPQQPYPQ NO: 62 | | |

All patents, patent applications, and other publications, including GenBank Accession Numbers, cited in this application are incorporated by reference in the entirety for all purposes.

---

INFORMAL SEQUENCE LISTING

---

13F6 Antibody Heavy Chain Variable Region DNA Sequencce
FR1-CDR1-FR2-CDR2-FR3-CDR3-FR4
CAGATCCAGTTGGTGCAGTCTGGACCTGAGCTGAAGAAGCCTGGAGAGACAGTCAAGATCTCCT
GCAAGGCTTCTGGTTATACCTTCACAGACTATTCAATGCACTGGGTGAGGCAGGCTCCAGGAAA
GGGTTTAAAGTGGATGGGCTGGATAAACACTGAGACTGGTGAGCCAACATATGCAGATGACTTC
AAGGGACGATTTGCCTTCTCTTTGGAAACCTCTGCCAGCACTGCCTATCTGCAGATCAACAACC
TCAAAAATGAGGACACGGCTACACATTTCTGTGCTCCAAGTGTTGCCTGGTTTGCTTACTGGGG
CCAAGGGACTCTGGTCACTGTCTCTACA SEQ ID NO: 2
13F6 Antibody Heavy Chain Variable Region Amino Acid Sequence
FR1-CDR1-FR2-CDR2-FR3-CDR3-FR4
QIQLVQSGPELKKPGETVKISCKASGYTFTDYSMHWVRQAPGKGLKWMGWINTETGEPTYADDF
KGRFAFSLETSASTAYLQINNLKNEDTATHFCAPSVAWFAYWGQGTLVTVST SEQ ID NO: 3
13F6 Antibody Heavy Chain CDR1 Amino Acid Sequence
DYSMH SEQ ID NO: 4
13F6 Antibody Heavy Chain CDR2 Amino Acid Sequence
WINTETGEPTYADDFKG SEQ ID NO: 5
13F6 Antibody Heavy Chain CDR3 Amino Acid Sequence
SVAWFAY SEQ ID NO: 6
13F6 Antibody Light Chain Variable Region DNA Sequence
FR1-CDR1-FR2-CDR2-FR3-CDR3-FR4
GATGTTTTGATGACCCAAACTCCACTCTCCCTGTCTGTCAGTCTTGGAGATCAGGCCTCCATCT
CTTGTAGATCTAGTCAGAGCATTGTACAGAGTAATGGAAACACCCATTTAGAATGGTTCTTACA
GAAACCAGGCCAGTCTCCAAAGCTCCTGATCTACAAAGTTTCCAACCGATTTTCTGGGGTCCCA
GACAGGTTCAGTGGCAGTGGATCAGGGACAGATTTCACACTCAAGATCAGCAGAGTGGAGGCTG
AGGATCTGGGAGTTTATTACTGTTTTCAAGGTTCACATGTTCCATTCACGTTCGGCTCGGGGAC
AAAGTTGGAAATAAAA SEQ ID NO: 7
13F6 Antibody Light Chain Variable Region Amino Acid Sequence
FR1-CDR1-FR2-CDR2-FR3-CDR3-FR4
DVLMTQTPLSLSVSLGDQASISCRSSQSIVQSNGNTHLEWFLQKPGQSPKLLIYKVSNRFSGVP
DRFSGSGSGTDFTLKISRVEAEDLGVYYCFQGSHVPFTFGSGTKLEIK SEQ ID NO: 8
13F6 Antibody Light Chain CDR1 Amino Acid Sequence
RSSQSIVQSNGNTHLE SEQ ID NO: 9
13F6 Antibody Light Chain CDR2 Amino Acid Sequence
KVSNRFS

INFORMAL SEQUENCE LISTING

SEQ ID NO: 10
13F6 Antibody Light Chain CDR3 Amino Acid Sequence
FQGSHVPFT

SEQ ID NO: 11
14G11 Antibody Heavy Chain Variable Region DNA Sequence
FR1-CDR1-FR2-CDR2-FR3-CDR3-FR4
CAGATCCAGTTGGTGCAGTCTGGACCTGAGATGAAGAAGCCTGGAGAGACAGTCAAGATTTTTT
GCAAGGCTTCTGGTTATACCCTCACAGACTATTCAATGCACTGGGTGAAGCAGGCTCCAGGAAA
GGGTTTAAAGTGGATGGGCTGGATAAACACTGAGACTGGTGAGCCAACATATGCAGATGACTTC
AAGGGACGGTGTGCCTTTTCTTTGGAAACCTCTGTCAGCACTGCCTTTTTGCAGATCAACAACC
TCAAAAATGAGGACATGGGAACATATTTCTGTGCCTCCTCTGGGGCCTGGTTTAGTTACTGGGG
CCAAGGGACTCTGGTCACTGTCTCTGCA SEQ ID NO: 12
14G11 Antibody Heavy Chain Variable Region Amino Acid Sequence
FR1-CDR1-FR2-CDR2-FR3-CDR3-FR4
QIQLVQSGPEMKKPGETVKIFCKASGYTLTDYSMHWVKQAPGKGLKWMGWINTETGEPTYADDF
KGRCAFSLETSVSTAFLQINNLKNEDMGTYFCASSGAWFSYWGQGTLVTVSA SEQ ID NO: 13
14G11 Antibody Heavy Chain CDR1 Amino Acid Sequence
DYSMH SEQ ID NO: 14
14G11 Antibody Heavy Chain CDR2 Amino Acid Sequence
WINTETGEPTYADDFKG SEQ ID NO: 15
14G11 Antibody Heavy Chain CDR3 Amino Acid Sequence
SGAWFSY SEQ ID NO: 16
14G11 Antibody Light Chain Variable Region DNA Sequence
FR1-CDR1-FR2-CDR2-FR3-CDR3-FR4
GATGTTTTGCTGACCCAAACTCCACTCTCCCTGCCTGTCAGTCTTGGAGATCAAGCCTCCATCT
CTTGCAGATCTAGTCAGACCATTGTACAAATTAATGGAAACACCCATTTAGAATGGTTCCTGCA
GAAACCAGGCCAGTCTCCAAAGCTCCTGATCTATAAAGTTTCCAACCGATTTTCTGGGGTCCCA
GACAGGTTCAGTGGCAGTGGATCAGGGACAGATTTCACACTCAAGATCAGCAGAGTGGAGGCTG
AGGATCTGGGAATTTATTACTGCTTTCAAGGTTCACATGTTCCATTCACGTTCGGCTCGGGGAC
AAAGTTGGAAATAAAA SEQ ID NO: 17
14G11 Antibody Light Chain Variable Region Amino Acid Sequence
FR1-CDR1-FR2-CDR2-FR3-CDR3-FR4
DVLLTQTPLSLPVSLGDQASISCRSSQTIVQINGNTHLEWFLQKPGQSPKLLIYKVSNRFSGVP
DRFSGSGSGTDFTLKISRVEAEDLGIYYCFQGSHVPFTFGSGTKLEIK SEQ ID NO: 18
14G11 Antibody Light Chain CDR1 Amino Acid Sequence
RSSQTIVQINGNTHLE SEQ ID NO: 19
14G11 Antibody Light Chain CDR2 Amino Acid Sequence
KVSNRFS SEQ ID NO: 20
14G11 Antibody Light Chain CDR3 Amino Acid Sequence
FQGSHVPFT SEQ ID NO: 21
Amino Acid Sequence for Epitope 1
Q(Q/L)PYPQ SEQ ID NO: 22
Amino Acid Sequence for Epitope 2
QQPYPQ SEQ ID NO: 23
Amino Acid Sequence for Epitope 3
QLPYPQ SEQ ID NO: 24
Amino Acid Sequence for Epitope 4
Q(Q/L)PYPQ(P/S)

| INFORMAL SEQUENCE LISTING |
| --- |

SEQ ID NO: 25
Amino Acid Sequence for Epitope 5
QQPYPQP

SEQ ID NO: 26
Amino Acid Sequence for Epitope 6
QLPYPQP

SEQ ID NO: 27
Amino Acid Sequence for Epitope 7
QQPYPQS

SEQ ID NO: 28
Amino Acid Sequence for Epitope 8
QLPYPQS

SEQ ID NO: 29
Amino Acid Sequence for Epitope 9
PQ(Q/L)PYPQ

SEQ ID NO: 30
Amino Acid Sequence for Epitope 10
PQQPYPQ

SEQ ID NO: 31
Amino Acid Sequence for Epitope 11
PQLPYPQ

[[SEQ ID NO: 32 accidentally skipped. SEQ ID NO: 32 skipped in Sequence Listing]]

SEQ ID NO: 33
33-mer Amino Acid Sequence Derived from α-2 gliadin
LQLQPFPQPQLPYPQPQLPYPQPQLPYPQPQPF

| SEQUENCE LISTING |
| --- |

<160> NUMBER OF SEQ ID NOS: 62

<210> SEQ ID NO 1
<211> LENGTH: 348
<212> TYPE: DNA
<213> ORGANISM: Mus musculus

<400> SEQUENCE: 1

```
cagatccagt tggtgcagtc tggacctgag ctgaagaagc ctggagagac agtcaagatc    60
tcctgcaagg cttctggtta taccttcaca gactattcaa tgcactgggt gaggcaggct   120
ccaggaaagg gtttaaagtg gatgggctgg ataaacactg agactggtga gccaacatat   180
gcagatgact tcaagggacg atttgccttc tctttggaaa cctctgccag cactgcctat   240
ctgcagatca acaacctcaa aaatgaggac acggctacac atttctgtgc tccaagtgtt   300
gcctggtttg cttactgggg ccaagggact ctggtcactg tctctaca              348
```

<210> SEQ ID NO 2
<211> LENGTH: 116
<212> TYPE: PRT
<213> ORGANISM: Mus musculus

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Arg Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr His Phe Cys
                 85                  90                  95

Ala Pro Ser Val Ala Trp Phe Ala Tyr Trp Gly Gln Gly Thr Leu Val
            100                 105                 110

Thr Val Ser Thr
        115

<210> SEQ ID NO 3
<211> LENGTH: 5
<212> TYPE: PRT
<213> ORGANISM: Mus musculus

<400> SEQUENCE: 3

Asp Tyr Ser Met His
1               5

<210> SEQ ID NO 4
<211> LENGTH: 17
<212> TYPE: PRT
<213> ORGANISM: Mus musculus

<400> SEQUENCE: 4

Trp Ile Asn Thr Glu Thr Gly Glu Pro Thr Tyr Ala Asp Asp Phe Lys
1               5                   10                  15

Gly

<210> SEQ ID NO 5
<211> LENGTH: 7
<212> TYPE: PRT
<213> ORGANISM: Mus musculus

<400> SEQUENCE: 5

Ser Val Ala Trp Phe Ala Tyr
1               5

<210> SEQ ID NO 6
<211> LENGTH: 336
<212> TYPE: DNA
<213> ORGANISM: Mus musculus

<400> SEQUENCE: 6
gatgttttga tgacccaaac tccactctcc ctgtctgtca gtcttggaga tcaggcctcc      60
atctcttgta gatctagtca gagcattgta cagagtaatg aaacaccca tttagaatgg     120 ttcttacaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgtt ttcaaggttc acatgttcca     300
ttcacgttcg gctcggggac aaagttggaa ataaaa                              336

<210> SEQ ID NO 7
<211> LENGTH: 112
<212> TYPE: PRT
<213> ORGANISM: Mus musculus

<400> SEQUENCE: 7

```
Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr His Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 8
<211> LENGTH: 16
<212> TYPE: PRT
<213> ORGANISM: Mus musculus

<400> SEQUENCE: 8

```
Arg Ser Ser Gln Ser Ile Val Gln Ser Asn Gly Asn Thr His Leu Glu
1               5                   10                  15
```

<210> SEQ ID NO 9
<211> LENGTH: 7
<212> TYPE: PRT
<213> ORGANISM: Mus musculus

<400> SEQUENCE: 9

```
Lys Val Ser Asn Arg Phe Ser
1               5
```

<210> SEQ ID NO 10
<211> LENGTH: 9
<212> TYPE: PRT
<213> ORGANISM: Mus musculus

<400> SEQUENCE: 10

```
Phe Gln Gly Ser His Val Pro Phe Thr
1               5
```

<210> SEQ ID NO 11
<211> LENGTH: 348
<212> TYPE: DNA
<213> ORGANISM: Mus musculus

<400> SEQUENCE: 11

```
cagatccagt tggtgcagtc tggacctgag atgaagaagc tggagagaca agtcaagatt      60
ttttgcaagg cttctggtta taccctcaca gactattcaa tgcactgggt gaagcaggct     120
ccaggaaagg gtttaaagtg gatgggctgg ataaacactg agactggtga gccaacatat     180
gcagatgact tcaagggacg gtgtgccttt tctttggaaa cctctgtcag cactgccttt     240
ttgcagatca caaccctcaa aaatgaggac atgggaacat atttctgtgc ctcctctggg     300
gcctggttta gttactgggg ccaagggact ctggtcactg tctctgca                  348
```

<210> SEQ ID NO 12
<211> LENGTH: 116
<212> TYPE: PRT
<213> ORGANISM: Mus musculus

<400> SEQUENCE: 12

Gln Ile Gln Leu Val Gln Ser Gly Pro Glu Met Lys Lys Pro Gly Glu
1               5                   10                  15

Thr Val Lys Ile Phe Cys Lys Ala Ser Gly Tyr Thr Leu Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Cys Ala Phe Ser Leu Glu Thr Ser Val Ser Thr Ala Phe
65                  70                  75                  80

Leu Gln Ile Asn Asn Leu Lys Asn Glu Asp Met Gly Thr Tyr Phe Cys
                85                  90                  95

Ala Ser Ser Gly Ala Trp Phe Ser Tyr Trp Gly Gln Gly Thr Leu Val
            100                 105                 110

Thr Val Ser Ala
        115

<210> SEQ ID NO 13
<211> LENGTH: 5
<212> TYPE: PRT
<213> ORGANISM: Mus musculus

<400> SEQUENCE: 13

Asp Tyr Ser Met His
1               5

<210> SEQ ID NO 14
<211> LENGTH: 17
<212> TYPE: PRT
<213> ORGANISM: Mus musculus

<400> SEQUENCE: 14

Trp Ile Asn Thr Glu Thr Gly Glu Pro Thr Tyr Ala Asp Asp Phe Lys
1               5                   10                  15

Gly

<210> SEQ ID NO 15
<211> LENGTH: 7
<212> TYPE: PRT
<213> ORGANISM: Mus musculus

<400> SEQUENCE: 15

Ser Gly Ala Trp Phe Ser Tyr
1               5

<210> SEQ ID NO 16
<211> LENGTH: 336
<212> TYPE: DNA
<213> ORGANISM: Mus musculus

<400> SEQUENCE: 16
gatgttttgc tgacccaaac tccactctcc ctgcctgtca gtcttggaga tcaagcctcc      60
atctcttgca gatctagtca gaccattgta caaattaatg gaaacaccca tttagaatgg     120
ttcctgcaga aaccaggcca gtctccaaag ctcctgatct ataaagtttc caaccgattt     180
tctggggtcc cagacaggtt cagtggcagt ggatcaggga cagatttcac actcaagatc     240
agcagagtgg aggctgagga tctgggaatt tattactgct ttcaaggttc acatgttcca     300
ttcacgttcg gctcggggac aaagttggaa ataaaa 336

<210> SEQ ID NO 17
<211> LENGTH: 112
<212> TYPE: PRT
<213> ORGANISM: Mus musculus

<400> SEQUENCE: 17

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Thr Ile Val Gln Ile
            20                  25                  30

Asn Gly Asn Thr His Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 18
<211> LENGTH: 16
<212> TYPE: PRT
<213> ORGANISM: Mus musculus

<400> SEQUENCE: 18

Arg Ser Ser Gln Thr Ile Val Gln Ile Asn Gly Asn Thr His Leu Glu
1               5                   10                  15

<210> SEQ ID NO 19
<211> LENGTH: 7
<212> TYPE: PRT
<213> ORGANISM: Mus musculus

<400> SEQUENCE: 19

Lys Val Ser Asn Arg Phe Ser
1               5

<210> SEQ ID NO 20
<211> LENGTH: 9
<212> TYPE: PRT
<213> ORGANISM: Mus musculus

<400> SEQUENCE: 20

Phe Gln Gly Ser His Val Pro Phe Thr
1               5

<210> SEQ ID NO 21
<211> LENGTH: 6
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: Xaa = Gln or Leu

<400> SEQUENCE: 21

Gln Xaa Pro Tyr Pro Gln
1               5

```
<210> SEQ ID NO 22
<211> LENGTH: 6
<212> TYPE: PRT
<213> ORGANISM: Mus musculus

<400> SEQUENCE: 22

Gln Gln Pro Tyr Pro Gln
1               5

<210> SEQ ID NO 23
<211> LENGTH: 6
<212> TYPE: PRT
<213> ORGANISM: Mus musculus

<400> SEQUENCE: 23

Gln Leu Pro Tyr Pro Gln
1               5

<210> SEQ ID NO 24
<211> LENGTH: 7
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: Xaa = Gln or Leu
<220> FEATURE:
<221> NAME/KEY: MISC_FEATURE
<222> LOCATION: (7)..(7)
<223> OTHER INFORMATION: Xaa = Pro or Ser

<400> SEQUENCE: 24

Gln Xaa Pro Tyr Pro Gln Xaa
1               5

<210> SEQ ID NO 25
<211> LENGTH: 7
<212> TYPE: PRT
<213> ORGANISM: Mus musculus

<400> SEQUENCE: 25

Gln Gln Pro Tyr Pro Gln Pro
1               5

<210> SEQ ID NO 26
<211> LENGTH: 7
<212> TYPE: PRT
<213> ORGANISM: Mus musculus

<400> SEQUENCE: 26

Gln Leu Pro Tyr Pro Gln Pro
1               5

<210> SEQ ID NO 27
<211> LENGTH: 7
<212> TYPE: PRT
<213> ORGANISM: Mus musculus

<400> SEQUENCE: 27

Gln Gln Pro Tyr Pro Gln Ser
1               5

<210> SEQ ID NO 28
<211> LENGTH: 7
<212> TYPE: PRT
```

```
<213> ORGANISM: Mus musculus

<400> SEQUENCE: 28

Gln Leu Pro Tyr Pro Gln Ser
1               5

<210> SEQ ID NO 29
<211> LENGTH: 7
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: Xaa = Gln or Leu

<400> SEQUENCE: 29

Pro Gln Xaa Pro Tyr Pro Gln
1               5

<210> SEQ ID NO 30
<211> LENGTH: 7
<212> TYPE: PRT
<213> ORGANISM: Mus musculus

<400> SEQUENCE: 30

Pro Gln Gln Pro Tyr Pro Gln
1               5

<210> SEQ ID NO 31
<211> LENGTH: 7
<212> TYPE: PRT
<213> ORGANISM: Mus musculus

<400> SEQUENCE: 31

Pro Gln Leu Pro Tyr Pro Gln
1               5

<210> SEQ ID NO 32

<400> SEQUENCE: 32

000

<210> SEQ ID NO 33
<211> LENGTH: 33
<212> TYPE: PRT
<213> ORGANISM: Unknown
<220> FEATURE:
<223> OTHER INFORMATION: Wheat gliadin protein

<400> SEQUENCE: 33

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 34
<211> LENGTH: 405
<212> TYPE: DNA
<213> ORGANISM: Mus musculus

<400> SEQUENCE: 34
atggcttggg tgtggaccct gctattcctg atggcagctg cccaaagtat ccaagcacag    60
```

-continued

```
atccagttgg tgcagtctgg acctgagctg aagaagcctg gagagacagt caagatctcc    120
tgcaaggctt ctggttatac cttcacagac tattcaatgc actgggtgag gcaggctcca    180
ggaaagggtt taaagtggat gggctggata acactgaga ctggtgagcc aacatatgca     240
gatgacttca agggacgatt tgccttctct ttggaaacct ctgccagcac tgcctatctg    300
cagatcaaca acctcaaaaa tgaggacacg gctacacatt tctgtgctcc aagtgttgcc    360
tggtttgctt actggggcca agggactctg gtcactgtct ctaca                    405
```

<210> SEQ ID NO 35
<211> LENGTH: 135
<212> TYPE: PRT
<213> ORGANISM: Mus musculus

<400> SEQUENCE: 35

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ser Met His Trp Val Arg Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

His Phe Cys Ala Pro Ser Val Ala Trp Phe Ala Tyr Trp Gly Gln Gly
        115                 120                 125

Thr Leu Val Thr Val Ser Thr
    130                 135
```

<210> SEQ ID NO 36
<211> LENGTH: 393
<212> TYPE: DNA
<213> ORGANISM: Mus musculus

<400> SEQUENCE: 36

```
atgaagttac tgttaggct gttggtgctg atgttctgga ttcctgcttc cagaagtgat     60
gttttgatga cccaaactcc actctccctg tctgtcagtc ttggagatca ggcctccatc    120
tcttgtagat ctagtcagag cattgtacag agtaatggaa acacccattt agaatggttc    180
ttacagaaac caggccagtc tccaaagctc ctgatctaca agtttccaa ccgattttct     240 ggggtcccag acaggttcag tggcagtgga tcagggacag atttcacact caagatcagc    300
agagtggagg ctgaggatct gggagtttat tactgttttc aaggttcaca tgttccattc    360
acgttcggct cggggacaaa gttggaaata aaa                                 393
```

<210> SEQ ID NO 37
<211> LENGTH: 131
<212> TYPE: PRT
<213> ORGANISM: Mus musculus

<400> SEQUENCE: 37

```
Met Lys Leu Pro Val Arg Leu Leu Val Leu Met Phe Trp Ile Pro Ala
1               5                   10                  15
```

Ser Arg Ser Asp Val Leu Met Thr Gln Thr Pro Leu Ser Leu Ser Val
            20                  25                  30

Ser Leu Gly Asp Gln Ala Ser Ile Ser Cys Arg Ser Ser Gln Ser Ile
        35                  40                  45

Val Gln Ser Asn Gly Asn Thr His Leu Glu Trp Phe Leu Gln Lys Pro
50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys
    130

<210> SEQ ID NO 38
<211> LENGTH: 405
<212> TYPE: DNA
<213> ORGANISM: Mus musculus

<400> SEQUENCE: 38
atggcttggg tgtggaccct tgctattcctg atggcagctg cccaaagtat ccaagcacag      60
atccagttgg tgcagtctgg acctgagatg aagaagcctg agagacagt caagattttt      120 tgcaaggctt ctggttatac cctcacagac tattcaatgc actgggtgaa gcaggctcca      180
ggaaagggtt taaagtggat gggctggata aacactgaga ctggtgagcc aacatatgca      240
gatgacttca agggacggtg tgccttttct ttggaaacct ctgtcagcac tgccttttg      300 cagatcaaca acctcaaaaa tgaggacatg ggaacatatt tctgtgcctc ctctggggcc      360
tggtttagtt actggggcca agggactctg gtcactgtct ctgca                     405

<210> SEQ ID NO 39
<211> LENGTH: 135
<212> TYPE: PRT
<213> ORGANISM: Mus musculus

<400> SEQUENCE: 39

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Met Lys Lys
            20                  25                  30

Pro Gly Glu Thr Val Lys Ile Phe Cys Lys Ala Ser Gly Tyr Thr Leu
        35                  40                  45

Thr Asp Tyr Ser Met His Trp Val Lys Gln Ala Pro Gly Lys Gly Leu
50                  55                  60

Lys Trp Met Gly Trp Ile Asn Thr Glu Thr Gly Glu Pro Thr Tyr Ala
65                  70                  75                  80

Asp Asp Phe Lys Gly Arg Cys Ala Phe Ser Leu Glu Thr Ser Val Ser
                85                  90                  95

Thr Ala Phe Leu Gln Ile Asn Asn Leu Lys Asn Glu Asp Met Gly Thr
            100                 105                 110

Tyr Phe Cys Ala Ser Ser Gly Ala Trp Phe Ser Tyr Trp Gly Gln Gly
        115                 120                 125

```
Thr Leu Val Thr Val Ser Ala
    130             135
```

<210> SEQ ID NO 40
<211> LENGTH: 393
<212> TYPE: DNA
<213> ORGANISM: Mus musculus

<400> SEQUENCE: 40

```
atgaagttgc ctgttaggct gttggtgctg atgttctgga ttcctgcctc cagtggtgat      60
gttttgctga cccaaactcc actctccctg cctgtcagtc ttggagatca agcctccatc     120
tcttgcagat ctagtcagac cattgtacaa attaatggaa acacccattt agaatggttc     180
ctgcagaaac caggccagtc tccaaagctc ctgatctata agtttccaac cgatttttct     240
ggggtcccag acaggttcag tgcagtggga tcaggacag atttcacact caagatcagc      300
agagtggagg ctgaggatct gggaatttat tactgctttc aaggttcaca tgttccattc     360
acgttcggct cggggacaaa gttggaaata aaa                                  393
```

<210> SEQ ID NO 41
<211> LENGTH: 131
<212> TYPE: PRT
<213> ORGANISM: Mus musculus

<400> SEQUENCE: 41

```
Met Lys Leu Pro Val Arg Leu Leu Val Leu Met Phe Trp Ile Pro Ala
1               5                   10                  15

Ser Ser Gly Asp Val Leu Leu Thr Gln Thr Pro Leu Ser Leu Pro Val
            20                  25                  30

Ser Leu Gly Asp Gln Ala Ser Ile Ser Cys Arg Ser Ser Gln Thr Ile
        35                  40                  45

Val Gln Ile Asn Gly Asn Thr His Leu Glu Trp Phe Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Ile Tyr Tyr Cys
            100                 105                 110

Phe Gln Gly Ser His Val Pro Phe Thr Phe Gly Ser Gly Thr Lys Leu
        115                 120                 125

Glu Ile Lys
    130
```

<210> SEQ ID NO 42
<211> LENGTH: 296
<212> TYPE: PRT
<213> ORGANISM: Mus musculus

<400> SEQUENCE: 42

```
Met Lys Thr Phe Leu Ile Leu Ala Leu Leu Ala Ile Val Ala Thr Thr
1               5                   10                  15

Ala Thr Thr Ala Val Arg Val Pro Val Pro Gln Pro Gln Pro Gln Asn
            20                  25                  30

Pro Ser Gln Pro Gln Pro Gln Arg Gln Val Pro Leu Val Gln Gln Gln
        35                  40                  45

Gln Phe Pro Gly Gln Gln Gln Phe Pro Pro Gln Gln Pro Tyr Pro
        50                  55                  60
```

```
Gln Pro Gln Pro Phe Pro Ser Gln Gln Pro Tyr Leu Gln Leu Gln Pro
 65                  70                  75                  80

Phe Pro Gln Pro Gln Pro Phe Pro Gln Leu Pro Tyr Pro Gln Pro
                 85                  90                  95

Pro Pro Phe Ser Pro Gln Gln Pro Tyr Pro Gln Pro Gln Pro Gln Tyr
            100                 105                 110

Pro Gln Pro Gln Gln Pro Ile Ser Gln Gln Ala Gln Gln Gln Gln
            115                 120                 125

Gln Gln Gln Gln Gln Gln Gln Gln Gln Gln Gln Gln Gln Ile Leu
            130                 135                 140

Pro Gln Ile Leu Gln Gln Leu Ile Pro Cys Arg Asp Val Val Leu
145                 150                 155                 160

Gln Gln His Asn Ile Ala His Ala Arg Ser Gln Val Leu Gln Gln Ser
                165                 170                 175

Thr Tyr Gln Pro Leu Gln Gln Leu Cys Cys Gln Gln Leu Trp Gln Ile
            180                 185                 190

Pro Glu Gln Ser Arg Cys Gln Ala Ile His Asn Val His Ala Ile
            195                 200                 205

Ile Leu His Gln Gln Gln Gln Gln Gln Pro Ser Ser Gln Val Ser
210                 215                 220

Leu Gln Gln Pro Gln Gln Tyr Pro Ser Gly Gln Gly Phe Phe Gln
225                 230                 235                 240

Pro Ser Gln Gln Asn Pro Gln Ala Gly Ser Val Gln Pro Gln Gln
                245                 250                 255

Leu Pro Gln Phe Glu Glu Ile Arg Asn Leu Ala Leu Gln Thr Leu Pro
                260                 265                 270

Arg Met Cys Asn Val Tyr Ile Pro Pro Tyr Cys Ser Thr Thr Thr Ala
                275                 280                 285

Pro Phe Gly Ile Phe Gly Thr Asn
    290                 295

<210> SEQ ID NO 43
<211> LENGTH: 290
<212> TYPE: PRT
<213> ORGANISM: Mus musculus

<400> SEQUENCE: 43

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Pro
                20                  25                  30

Gly Gln Gln Gln Pro Phe Pro Pro Gln Gln Pro Tyr Pro Gln Pro Gln
            35                  40                  45

Pro Phe Pro Ser Gln Gln Pro Tyr Leu Gln Leu Gln Pro Phe Pro Gln
         50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Pro Phe Arg Pro Gln Gln Pro Tyr Pro
                85                  90                  95

Gln Ser Gln Pro Gln Tyr Ser Gln Pro Gln Pro Ile Ser Gln Gln
            100                 105                 110

Gln Gln Gln Gln Gln Gln Gln Gln Gln Lys Gln Gln Gln Gln
            115                 120                 125

Gln Gln Gln Ile Leu Gln Gln Ile Leu Gln Gln Gln Leu Ile Pro Cys
```

```
                    130                 135                 140
Arg Asp Val Val Leu Gln Gln His Ser Ile Ala Tyr Gly Ser Ser Gln
145                 150                 155                 160

Val Leu Gln Gln Ser Thr Tyr Gln Leu Val Gln Gln Leu Cys Cys Gln
                165                 170                 175

Gln Leu Trp Gln Ile Pro Glu Gln Ser Arg Cys Gln Ala Ile His Asn
            180                 185                 190

Val Val His Ala Ile Ile Leu His Gln Gln Gln Gln Gln Gln Gln Gln
        195                 200                 205

Gln Gln Gln Gln Pro Leu Ser Gln Val Ser Phe Gln Gln Pro Gln Gln
    210                 215                 220

Gln Tyr Pro Ser Gly Gln Gly Ser Phe Gln Pro Ser Gln Gln Asn Pro
225                 230                 235                 240

Gln Ala Gln Gly Ser Val Gln Pro Gln Gln Leu Pro Gln Phe Glu Glu
                245                 250                 255

Ile Arg Asn Leu Ala Leu Glu Thr Leu Pro Ala Met Cys Asn Val Tyr
            260                 265                 270

Ile Pro Pro Tyr Cys Thr Ile Ala Pro Val Gly Ile Phe Gly Thr Asn
        275                 280                 285

Tyr Arg
    290

<210> SEQ ID NO 44
<211> LENGTH: 10
<212> TYPE: PRT
<213> ORGANISM: Mus musculus

<400> SEQUENCE: 44

Ala Gln Gln Gln Gln Gln Gln Gln Gln
1               5                   10

<210> SEQ ID NO 45
<211> LENGTH: 5
<212> TYPE: PRT
<213> ORGANISM: Mus musculus

<400> SEQUENCE: 45

Gln Gln Pro Phe Pro
1               5

<210> SEQ ID NO 46
<211> LENGTH: 10
<212> TYPE: PRT
<213> ORGANISM: Mus musculus

<400> SEQUENCE: 46

Gln Gln Gln Gln Gln Gln Gln Gln Gln
1               5                   10

<210> SEQ ID NO 47
<211> LENGTH: 6
<212> TYPE: PRT
<213> ORGANISM: Mus musculus

<400> SEQUENCE: 47

Gln Pro Gln Leu Pro Tyr
1               5

<210> SEQ ID NO 48
<211> LENGTH: 6
```

```
<212> TYPE: PRT
<213> ORGANISM: Mus musculus

<400> SEQUENCE: 48

Gln Pro Gln Gln Pro Tyr
1               5

<210> SEQ ID NO 49
<211> LENGTH: 6
<212> TYPE: PRT
<213> ORGANISM: Mus musculus

<400> SEQUENCE: 49

Gln Pro Gln Leu Pro Phe
1               5

<210> SEQ ID NO 50
<211> LENGTH: 10
<212> TYPE: PRT
<213> ORGANISM: Mus musculus

<400> SEQUENCE: 50

Pro Gln Gln Pro Tyr Pro Gln Pro Gln Pro
1               5                   10

<210> SEQ ID NO 51
<211> LENGTH: 10
<212> TYPE: PRT
<213> ORGANISM: Mus musculus

<400> SEQUENCE: 51

Pro Gln Pro Gln Leu Pro Tyr Pro Gln Pro
1               5                   10

<210> SEQ ID NO 52
<211> LENGTH: 10
<212> TYPE: PRT
<213> ORGANISM: Mus musculus

<400> SEQUENCE: 52

Gln Leu Pro Tyr Pro Gln Pro Gln Leu Pro
1               5                   10

<210> SEQ ID NO 53
<211> LENGTH: 10
<212> TYPE: PRT
<213> ORGANISM: Mus musculus

<400> SEQUENCE: 53

Pro Gln Leu Pro Tyr Pro Gln Pro Gln Pro
1               5                   10

<210> SEQ ID NO 54
<211> LENGTH: 10
<212> TYPE: PRT
<213> ORGANISM: Mus musculus

<400> SEQUENCE: 54

Pro Pro Gln Gln Pro Tyr Pro Gln Pro Gln
1               5                   10

<210> SEQ ID NO 55
<211> LENGTH: 10
<212> TYPE: PRT
<213> ORGANISM: Mus musculus
```

<400> SEQUENCE: 55

Ser Pro Gln Gln Pro Tyr Pro Gln Pro Gln
1               5                   10

<210> SEQ ID NO 56
<211> LENGTH: 10
<212> TYPE: PRT
<213> ORGANISM: Mus musculus

<400> SEQUENCE: 56

Gln Pro Gln Leu Pro Tyr Pro Gln Pro Gln
1               5                   10

<210> SEQ ID NO 57
<211> LENGTH: 10
<212> TYPE: PRT
<213> ORGANISM: Mus musculus

<400> SEQUENCE: 57

Pro Gln Leu Pro Tyr Pro Gln Pro Gln Leu
1               5                   10

<210> SEQ ID NO 58
<211> LENGTH: 10
<212> TYPE: PRT
<213> ORGANISM: Mus musculus

<400> SEQUENCE: 58

Pro Gln Gln Pro Tyr Pro Gln Ser Gln Pro
1               5                   10

<210> SEQ ID NO 59
<211> LENGTH: 10
<212> TYPE: PRT
<213> ORGANISM: Mus musculus

<400> SEQUENCE: 59

Pro Pro Gln Leu Pro Tyr Pro Gln Pro Pro
1               5                   10

<210> SEQ ID NO 60
<211> LENGTH: 10
<212> TYPE: PRT
<213> ORGANISM: Mus musculus

<400> SEQUENCE: 60

Pro Phe Pro Pro Gln Gln Pro Tyr Pro Gln
1               5                   10

<210> SEQ ID NO 61
<211> LENGTH: 10
<212> TYPE: PRT
<213> ORGANISM: Mus musculus

<400> SEQUENCE: 61

Tyr Pro Gln Pro Gln Leu Pro Tyr Pro Gln
1               5                   10

<210> SEQ ID NO 62
<211> LENGTH: 10
<212> TYPE: PRT
<213> ORGANISM: Mus musculus

```
<400> SEQUENCE: 62

Pro Phe Arg Pro Gln Gln Pro Tyr Pro Gln
1               5                   10
```

What is claimed is:

1. An isolated antibody or antibody fragment comprising (1) a heavy chain variable region comprising a CDR1 of SEQ ID NO:3, a CDR2 of SEQ ID NO:4, and a CDR3 of SEQ ID NO:5 and a light chain variable region comprising a CDR1 of SEQ ID NO:8, a CDR2 of SEQ ID NO:9, and a CDR3 of SEQ ID NO:10; or (2) a heavy chain variable region comprising a CDR1 of SEQ ID NO:13, a CDR2 of SEQ ID NO:14, and a CDR3 of SEQ ID NO: 15 and a light chain variable region comprising a CDR1 of SEQ ID NO: 18, a CDR2 of SEQ ID NO:19, and a CDR3 of SEQ ID NO:20, wherein the antibody or antibody fragment binds to gliadin at an epitope defined by the amino acid sequence set forth in any one of SEQ ID NOs:21-32.

2. The isolated antibody or antibody fragment of claim 1, wherein the heavy chain variable region has an amino acid sequence of SEQ ID NO:2, and wherein the light chain variable region has an amino acid sequence of SEQ ID NO:7.

3. The isolated antibody or antibody fragment of claim 1, wherein the heavy chain variable region has an amino acid sequence of SEQ ID NO:12, and wherein the light chain variable region has an amino acid sequence of SEQ ID NO:17.

4. The isolated antibody or antibody fragment of claim 1, wherein the gliadin is wheat gliadin, barley hordein, or rye secalin.

5. The isolated antibody or antibody fragment of claim 1, wherein the antibody is a single-chain Fv (scFV).

6. The isolated antibody or antibody fragment of claim 1, wherein the antibody is an IgG.

7. The isolated antibody or antibody fragment of claim 1, wherein the antibody is linked to a detectable agent.

8. A kit for detecting gliadin comprising an antibody or antibody fragment of claim 1.

9. The kit of claim 8, further comprising a solution for dissolving a test sample.

10. The kit of claim 8, wherein the antibody or antibody fragment is linked to a detectable agent.

11. The kit of claim 8, further comprising a positive control containing gliadin.

12. An isolated nucleic acid comprising a polynucleotide sequence encoding an antibody heavy chain variable region comprising a CDR1 of SEQ ID NO:3, a CDR2 of SEQ ID NO:4, and a CDR3 of SEQ ID NO: 5; an antibody light chain variable region comprising a CDR1 of SEQ ID NO:8, a CDR2 of SEQ ID NO:9, and a CDR3 of SEQ ID NO:10; an antibody a heavy chain variable region comprising a CDR1 of SEQ ID NO: 13, a CDR2 of SEQ ID NO: 14, and a CDR3 of SEQ ID NO: 15; or an antibody light chain variable region comprising a CDR1 of SEQ NO:18, a CDR2 of SEQ ID NO:19, and a CDR3 of SEQ ID NO:20.

13. The nucleic acid of claim 12, wherein the polynucleotide sequence encodes (1) an antibody heavy chain variable region having the amino acid sequence of SEQ ID NO:2 or 12; or (2) an antibody light chain variable region having the amino acid sequence of SEQ ID NO:7 or 17.

14. The nucleic acid of claim 12, wherein the polynucleotide sequence is SEQ ID NO:1, 6, 11, or 16.

15. The nucleic acid of claim 14, further comprising a promoter operably linked to the polynucleotide sequence.

16. A method of detecting gliadin in a test sample comprising contacting the sample with the antibody or antibody fragment of claim 1.

17. The method of claim 16, wherein the sample is a food or beverage sample.

* * * * *

UNITED STATES PATENT AND TRADEMARK OFFICE
CERTIFICATE OF CORRECTION

PATENT NO. : 11,214,612 B2
APPLICATION NO. : 16/342031
DATED : January 4, 2022
INVENTOR(S) : Jingqing Zhang et al.

Page 1 of 1

It is certified that error appears in the above-identified patent and that said Letters Patent is hereby corrected as shown below:

In the Specification

Column 18, Line 7, "$^{35}I$" should be --$^{35}S$--.

Column 19, Line 63, "byway" should be --by way--.

Column 19, Line 64, "byway" should be --by way--.

Signed and Sealed this
First Day of March, 2022

Drew Hirshfeld
*Performing the Functions and Duties of the
Under Secretary of Commerce for Intellectual Property and
Director of the United States Patent and Trademark Office*